US010085485B2

(12) United States Patent
Hunt et al.

(10) Patent No.: US 10,085,485 B2
(45) Date of Patent: Oct. 2, 2018

(54) AEROSOL DELIVERY DEVICE WITH A RESERVOIR HOUSING AND A VAPORIZER ASSEMBLY

(71) Applicant: RAI Strategic Holdings, Inc., Winston-Salem, NC (US)

(72) Inventors: Eric Taylor Hunt, Pfafftown, NC (US); Timothy Brian Nestor, Advance, NC (US); Paul Andrew Brinkley, Winston-Salem, NC (US); Stephen Benson Sears, Siler City, NC (US); John DePiano, Burlington, MA (US); Matthew C. Ebbs, Newton-Highlands, MA (US); Kristen Dodds Weight, Stow, MA (US); Michael F. Davis, Clemmons, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 15/202,947

(22) Filed: Jul. 6, 2016

(65) Prior Publication Data

US 2018/0007962 A1 Jan. 11, 2018

(51) Int. Cl.
| | | |
|---|---|---|
| *A24F 13/00* | (2006.01) | |
| *A24F 47/00* | (2006.01) | |
| *F16J 15/02* | (2006.01) | |
| *B65D 25/38* | (2006.01) | |

(52) U.S. Cl.
CPC ............ *A24F 47/008* (2013.01); *B65D 25/38* (2013.01); *F16J 15/021* (2013.01)

(58) Field of Classification Search
CPC ....................................... A24F 47/00
USPC .................................. 131/328, 329
See application file for complete search history.

(56) References Cited

U.S. PATENT DOCUMENTS

| | | | |
|---|---|---|---|
| 1,771,366 | A | 7/1930 | Wyss et al. |
| 2,057,353 | A | 10/1936 | Whittemore, Jr. |
| 2,104,266 | A | 1/1938 | McCormick |
| 3,200,819 | A | 8/1965 | Gilbert |
| 4,284,089 | A | 8/1981 | Ray |
| 4,303,083 | A | 12/1981 | Burruss, Jr. |
| 4,735,217 | A | 4/1988 | Gerth et al. |
| 4,848,374 | A | 7/1989 | Chard et al. |

(Continued)

FOREIGN PATENT DOCUMENTS

| | | |
|---|---|---|
| AU | 276250 | 7/1965 |
| CA | 2 641 869 | 5/2010 |

(Continued)

*Primary Examiner* — Phuong Dinh
(74) *Attorney, Agent, or Firm* — Womble Bond Dickinson (US) LLP

(57) ABSTRACT

The present disclosure relates to an aerosol delivery device that includes a reservoir housing that defines a mouthpiece channel. The aerosol delivery device includes a sealing member configured to be received within the reservoir housing to define a reservoir chamber configured to retain an aerosol precursor composition therein. The aerosol delivery device also includes a substrate member that is configured to be received within the reservoir housing and to be directly engaged with a vaporizing assembly for forming an aerosol. The reservoir housing, sealing member, substrate member, and/or vaporizing assembly can be used for forming aerosols with precise and reproducible compositions.

20 Claims, 15 Drawing Sheets

(56) References Cited

U.S. PATENT DOCUMENTS

| | | |
|---|---|---|
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0031968 A1 | 2/2010 | Sheikh et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0298905 A1 | 11/2013 | Levin et al. |
| 2013/0306084 A1 | 11/2013 | Flick |
| 2013/0319438 A1 | 12/2013 | Liu |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0332021 A1 | 11/2014 | Li et al. |
| 2014/0345631 A1 | 11/2014 | Bowen et al. |

(56) References Cited

U.S. PATENT DOCUMENTS

| | | | |
|---|---|---|---|
| 2015/0053217 | A1 | 2/2015 | Steingraber et al. |
| 2016/0007654 | A1* | 1/2016 | Zhu .................. A24F 47/008 131/328 |
| 2016/0121058 | A1 | 5/2016 | Chen |
| 2016/0249684 | A1* | 9/2016 | Liu .................. A24F 47/008 131/328 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |

* cited by examiner

1300

1302 — providing a reservoir chamber defined, in part, by an outer housing formed of a wall and a central tube interior to the outer housing and formed of a wall, the outer housing having a closed mouthend and an opposing connecting end, the central tube having a first end opening through the closed mouthend of the outer housing and a second opposing open end 1304 — dispensing an aerosol precursor composition within the reservoir chamber and between the wall of the outer housing and the wall of the central tube from the connecting end of the outer housing 1306 — inserting a sealing member into the outer housing from the connecting end of the outer housing, the sealing member having a central orifice, so as to engage a peripheral portion of the sealing member with the wall of the outer housing and the central orifice of the sealing member with the second open end of the central tube in a sealing arrangement 1308 — inserting a substrate member adjacent to the sealing member within the outer housing from the connecting end of the outer housing

AEROSOL DELIVERY DEVICE WITH A RESERVOIR HOUSING AND A VAPORIZER ASSEMBLY

FIELD OF THE DISCLOSURE

The present disclosure relates to aerosol delivery devices, and more particularly to aerosol delivery devices that include a reservoir housing and a vaporizing assembly, which may utilize electrical power to heat an aerosol precursor composition for the production of an aerosol. The aerosol precursor composition, which may incorporate materials and/or components that may be made or derived from tobacco or otherwise incorporate tobacco, is heated by the vaporizing assembly to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al.; 2014/0283859 to Minskoff et al.; 2015/0335070 to Sears et al.; 2015/0335071 to Brinkley et al.; 2016/0007651 to Ampolini et al.; as well as U.S. patent application Ser. No. 14/465,167 to Worm et al., filed Aug. 21, 2014; all of which are incorporated herein by reference.

Certain existing embodiments of aerosol delivery devices include a control body (i.e., a power source assembly) and a cartridge (i.e., a reservoir housing). A power source (e.g., a battery) may be positioned in the control body, and an aerosol precursor composition may be retained and/or stored within the cartridge. The cartridge and the control body may engage one another to define an elongated tubular configuration. However, certain other form factors for aerosol delivery devices and other aerosol precursor composition storage arrangements may be desirable.

SUMMARY OF THE DISCLOSURE

The present disclosure relates to aerosol delivery devices that may be used in formation of vapor. An aerosol delivery device as described herein may be beneficial in providing for precise control over aerosol composition and/or secured storage of any aerosol precursor composition.

In some aspects, the present disclosure provides an aerosol delivery device that includes a reservoir housing having a mouthend and a connecting end and being formed of an outer wall.

The aerosol delivery device further includes a mouthpiece channel within the reservoir housing that is formed of an outer wall. The mouthpiece channel extends at least partially along the length of the reservoir housing from the mouthend of the reservoir housing to a terminal end. Further, the mouthpiece channel may have an opening at the mouthend of the reservoir housing and another opening at the terminal end of the mouthpiece channel.

According to some aspects, the aerosol delivery device may include a sealing member in a sealing arrangement with the reservoir housing outer wall and the mouthpiece channel outer wall so as to define a reservoir chamber configured to retain an aerosol precursor composition therein. The sealing member may include at least one aerosol precursor composition orifice configured for flow therethrough of aerosol precursor composition and may also include a sealing member vapor orifice in communication with the opening at the terminal end of the mouthpiece channel.

In some aspects, the aerosol delivery device includes a substrate member disposed adjacent the sealing member so as to be in fluid communication with the reservoir chamber through the sealing member. The substrate member may further include a substrate member vapor orifice that is in communication with the sealing member vapor orifice.

According to some aspects, the aerosol delivery device may include a vaporizing assembly that includes a liquid transport element in fluid communication with the substrate member. The vaporizing assembly may also include a heating element in a heating arrangement with the liquid transport element.

The vaporizing assembly may further include at least one power connector that operably engages the heating element. Additionally, the aerosol delivery device may include a connector housing that is configured to operably engage a power source. In some aspects, the vaporizing assembly may be arranged at least partially within the connector housing. According to some aspects, the aerosol delivery device may further include an atomizer housing, which includes a vaporizing chamber. In some aspects, the liquid transfer element and the heating element may be disposed within the vaporizing chamber. Additionally, the vaporizing chamber may be in fluid communication with the substrate member vapor orifice. Further, the atomizer housing may be operably engaged with the connector housing. In some aspects, the sealing member vapor orifice may be configured to provide for fluid communication between the mouthpiece channel and the vaporizing assembly. Further, the sealing member vapor orifice may be configured to receive at least a portion of the mouthpiece channel therethrough.

In some aspects, the sealing member may include a sealing element configured to be operably engaged with the outer wall of the reservoir housing. For example, the sealing element may include a flange portion configured to be operably engaged with the outer wall of the reservoir housing. According to some aspects, the sealing element may include a flange portion configured to be operably engaged with the outer wall off the mouthpiece channel. The mouthpiece channel and the reservoir housing may be substantially coaxial with respect to one another.

According to some aspects, the reservoir housing may further include at least one sealing member support that extends along a direction substantially parallel to a longitudinal axis of the reservoir housing. Additionally, the at least one sealing member support may have a terminal end. In some aspects, the terminal end of the mouthpiece channel may extend beyond the terminal end of the sealing member support from the mouthend of the reservoir housing. The terminal end of the sealing member support may directly engage the sealing member.

In some aspects, the present disclosure may provide a liquid storage tank for an aerosol delivery device. The liquid storage tank may include an outer housing formed of a wall. The outer housing may include a closed mouthend and an opposing end. According to some aspects, the liquid storage tank includes a central tube interior to the outer housing and formed of a wall. The central tube may also include a first end opening through the closed mouthend of the outer housing and a second, opposing open end. In some aspects, the liquid storage tank includes a sealing member that sealingly engages the wall of the outer housing and has a central orifice aligned with the second open end of the central tube in a sealing arrangement with the wall of the central tube. Further, the liquid storage tank may include a substrate member adjacent the sealing member. Additionally, the wall of the outer housing, the wall of the central tube, and the sealing member may define a reservoir chamber configured for storage of an aerosol precursor composition. The sealing member may further include at least one orifice configured for passage of the aerosol precursor composition between the reservoir chamber and the substrate member.

According to some aspects, the present disclosure may provide a method of manufacturing a liquid storage tank for an aerosol delivery device. The method may include providing a reservoir chamber that may be defined, in part, by an outer housing formed of a wall and a central tube interior to the outer housing and formed of a wall. The outer housing may include a closed mouthend and an opposing connecting end. Additionally, the central tube may include a first end opening through the closed mouthend of the outer housing. Further, the central tube may include a second opposing open end. The method may further include dispensing an aerosol precursor composition within the reservoir chamber. In particular, the method may include dispensing the aerosol precursor composition between the wall of the outer housing and the wall of the central tube from the connecting end of the outer housing. In some aspects, the method may include inserting a sealing member into the outer housing from the connecting end of the outer housing. The sealing member includes a sealing member vapor orifice, and inserting the sealing member into the outer housing may include engaging a peripheral portion of the sealing member with the wall of the outer housing and engaging the sealing member vapor orifice with the second open end of the central tube in a sealing arrangement. According to some aspects, the method may include inserting a substrate member adjacent to the sealing member within the outer housing from the connecting end of the outer housing. Further, the substrate member may include a substrate member vapor orifice.

According to some aspects, the method further includes inserting at least a portion of a vaporizing assembly within the outer housing from the connecting end of the outer housing. The vaporizing assembly may include a liquid transport element. Further, inserting at least a portion of the vaporizing assembly within the outer housing may provide for engaging the liquid transport element with the substrate member disposed within the outer housing. In some aspects, the vaporizing assembly includes a heating element in a heating arrangement with the liquid transport element.

In some aspects, the sealing member further includes a substrate engaging element that extends from the sealing member and along a direction substantially parallel to a longitudinal axis of the outer housing. According to some aspects, inserting the substrate member adjacent to the sealing member within the outer housing includes inserting the substrate engaging element through at least a portion of the substrate member vapor orifice so as to provide for fluid communication between the first end opening of the central tube and the substrate member vapor orifice. Additionally, the outer housing further includes at least one sealing member support extending along a direction substantially parallel to a longitudinal axis of the outer housing and having a terminal end. According to some aspects, inserting the sealing member into the outer housing from the connecting end of the outer housing further includes inserting the sealing member so as to directly engage a portion of the sealing member with the terminal end of the sealing member support. Further, the second opposing open end of the central tube extends beyond the terminal end of the sealing member support from the closed mouthend of the outer housing.

It will be appreciated that the above Summary is provided merely for purposes of summarizing some example aspects so as to provide a basic understanding of some aspects of the disclosure. As such, it will be appreciated that the above described example aspects are merely examples of some aspects and should not be construed to narrow the scope or spirit of the disclosure in any way. It will be appreciated that the scope of the disclosure encompasses many potential aspects, some of which will be further described below, in addition to those here summarized. Further, other features, aspects, and advantages of the disclosure will be apparent from a reading of the following detailed description taken in conjunction with the accompanying drawings which illustrate, by way of example, the principles of the described aspects.

BRIEF DESCRIPTION OF THE FIGURES

In order to assist the understanding of aspects of the disclosure, reference will now be made to the appended drawings, which are not necessarily drawn to scale and in which like reference numerals refer to like elements. The drawings are exemplary only, and should not be construed as limiting the disclosure.

FIG. 13 is a schematic block diagram of a method for assembling an aerosol delivery device according to an example aspect of the present disclosure;

DETAILED DESCRIPTION

Figure 1:
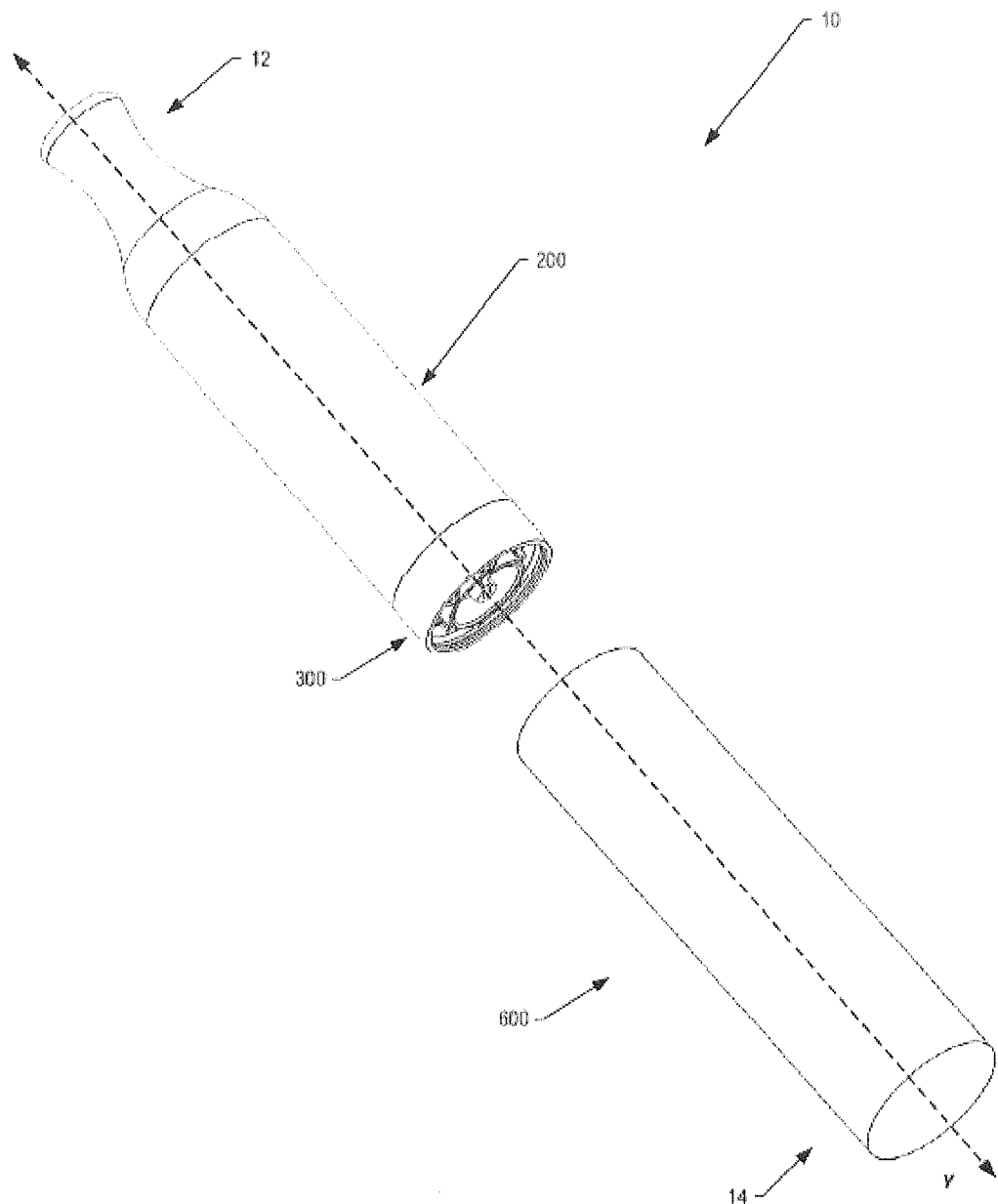
FIG. 1 is a perspective view of an aerosol delivery device according to an example aspect of the present disclosure.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors/aerosols resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article (e.g., a cigarette, cigar or pipe that is employed by lighting with a flame and used by inhaling tobacco that is subsequently burned and/or combusted), draw on one end of that piece for inhalation of aerosol produced by that piece, take or draw puffs at selected intervals of time, and the like. The devices described herein, however, are not limited to devices that are substantially shaped and dimensioned as a traditional cigarette. Rather, the present devices may take on any shape and can be substantially larger than a traditional cigarette. In certain preferred aspects, the device may be sufficiently compact to be considered "hand-held" devices.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. In exemplary embodiments, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within a single housing. Alternatively, an aerosol delivery device can comprise two or more housings that are joined and are separable. For example, an aerosol delivery device can possess two bodies that are substantially axially aligned when joined and can include at one end, a control body comprising a housing containing one or more components (e.g., a battery and various electronics for controlling the operation of that article), and at the other end and removably attached thereto, an outer body or shell containing aerosol forming components (e.g., one or more aerosol precursor components, such as flavors and aerosol formers, one or more heaters, and/or one or more wicks). Aerosol delivery devices described herein, however, are not limited to devices that include two bodies that are substantially axially aligned when joined together.

Aerosol delivery devices of the present disclosure can be formed of an outer housing or shell that is not substantially tubular in shape but may be formed to substantially greater dimensions—i.e., be substantially "palm-sized" for being held in the palm of a user. The housing or shell can be configured to include a mouthpiece and/or may be configured to receive a separate shell (e.g., a cartridge) that can include consumable elements, such as a liquid aerosol precursor composition, and can include a vaporizer or atomizer.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure. One example aspect of an aerosol delivery device 10 according to the present disclosure is provided in FIG. 1. The aerosol delivery device 10 can include a reservoir housing 200, a vaporizing assembly 300 and a power source assembly 600, which may be operably engaged with one another. In one aspect, the reservoir housing 200 and the vaporizing assembly 300 can be permanently or detachably engaged in a functioning relationship. Operable engagement between the reservoir housing 200 and the vaporizing assembly 300 can be press fit, threaded, interference fit, magnetic, ultrasonic welded, and/or the like. In some aspects, the vaporizing assembly 300 and the power source assembly 600 may be directly and operably engaged with one another. For example, the vaporizing assembly 300 and the power source assembly 600 may be detachable from one another and mechanically engaged in a functioning relationship. In some aspects, the vaporizing assembly 300 and the power source assembly 600 may be engaged with one another in a functioning relationship such that the power source assembly 600 provides electrical power to the vaporizing assembly 300 and/or additional control functionality as described in greater detail herein. According to another aspect, as shown in FIG. 2, a reservoir housing 200 may be operably engaged with a power source assembly 600 and may include a vaporizing assembly therein configured to operably engage a power source disposed in the power source assembly 600. Alternatively, the vaporizing assembly may be disposed within the power source assembly 600 and may be configured to operably engage a reservoir housing that is detachably engaged in a functioning relationship with the power source assembly 600. Further aspects of such devices are described in U.S. patent application Ser. No. 14/465,167 to Worm et al., filed Aug. 21, 2014, and Ser. No. 14/981,051 to Phillips et al., filed Dec. 28, 2015, the disclosures of which are incorporated herein by reference.

According to some aspects, one or any of the reservoir housing 200, the vaporizing assembly 300, and/or the power source assembly 600 may be referred to as being disposable or as being reusable. For example, the power source assembly 600 may include a replaceable power source such as replaceable battery. In another aspect, the power source assembly may include a rechargeable battery, and thus may be combined with any type of recharging technology, including connection to a typical electrical outlet, connection to a car charger (e.g., a cigarette lighter receptacle), and/or connection to a computer, such as through a universal serial bus (USB) cable. For example, an adaptor including a USB connector at one end and a control body connector at an opposing end is disclosed in U.S. Pat. App. Pub. No. 2014/0261495 to Novak et al., which is incorporated herein by reference in its entirety. Examples of useful rechargeable power sources include lithium ion batteries, and more particularly, lithium polymer batteries. Additional examples of batteries that can be used according to the disclosure are described in U.S. Pat. App. Pub. No. 2010/0028766 to Peckerar et al., the disclosure of which is incorporated herein by reference in its entirety.

In another aspect, the reservoir housing 200 and the vaporizing assembly 300 may be securely attached and/or affixed to one another to form a disposable single-use cartridge. For example, the reservoir housing 200 may include a limited amount of aerosol precursor composition therein to provide for many of the sensations (e.g., inhalation and exhalation rituals, types of tastes or flavors, organoleptic effects, etc.) of smoking a particular amount of traditional types of smoking articles (e.g., cigarettes, cigars, pipes, etc.). In some aspects, the reservoir housing 200 may include a particular amount of aerosol precursor composition therein equivalent to the amount of traditional types of smoking articles one would consume to obtain the sensations of smoking a typical amount of traditional types of smoking articles (e.g., a typical package of cigarettes—i.e., twenty (20) cigarettes). Additionally or alternatively, the reservoir housing 200 and the vaporizing assembly 300 may be securely engaged with one another so as to prevent tampering and/or manipulation of the aerosol precursor composition stored within a reservoir chamber 210.

Figure 2:
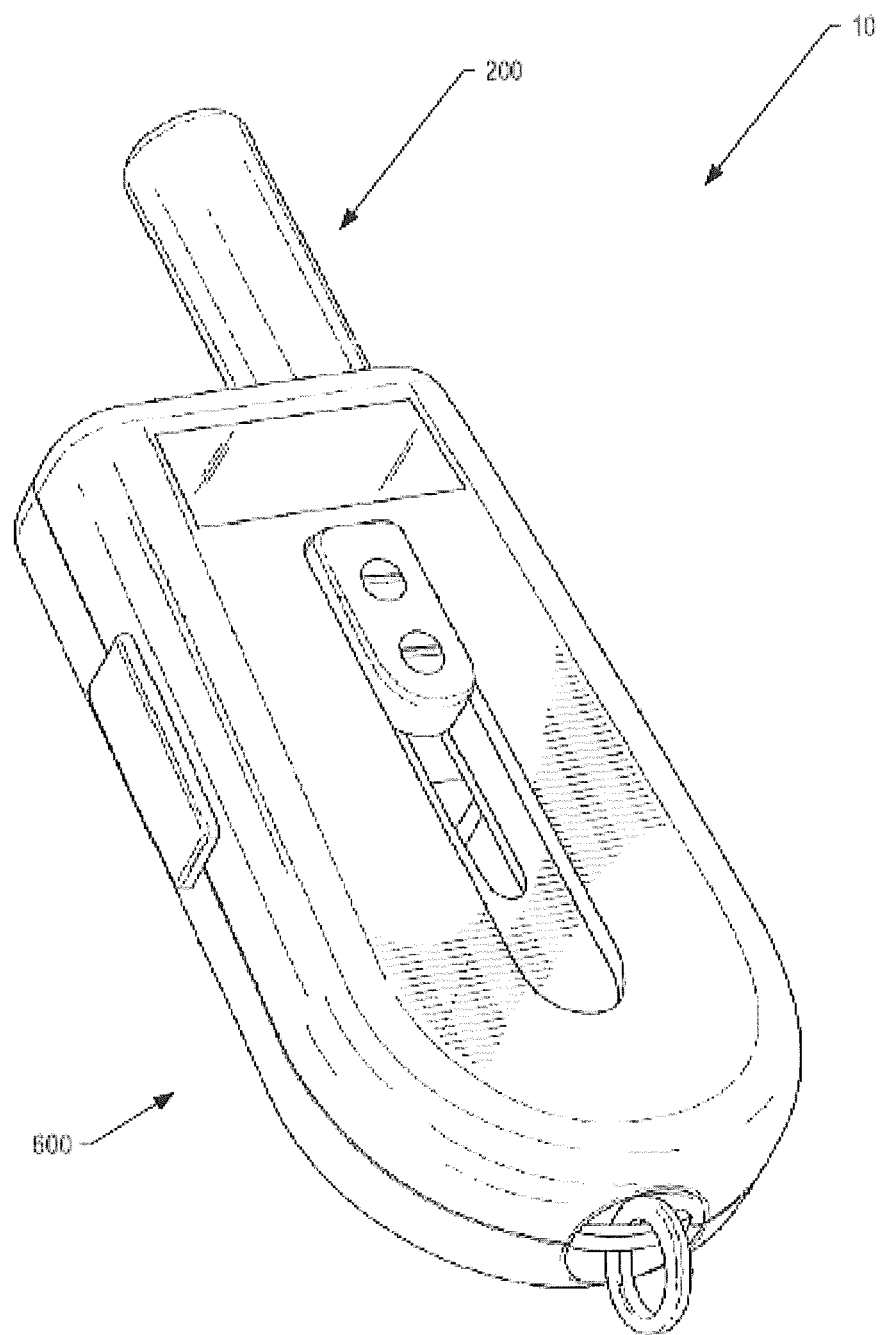
FIG. 2 is a perspective view of an aerosol delivery device according to another example aspect of the present disclosure.

As shown in FIG. 1, the aerosol delivery device 10 defines a longitudinal axis Y that extends from a first end 12 to an opposing second end 14 of the aerosol delivery device 10. The aerosol delivery device 10 may be substantially rod-like or substantially tubular or cylindrically shaped in some aspects. Although the aerosol delivery device 10 is illustrated as being substantially tubular and cylindrical in shape in FIG. 1, other suitable shapes and dimensions (e.g., a rectangular or triangular cross-section or the like) are also encompassed by the present disclosure.

Figure 3:
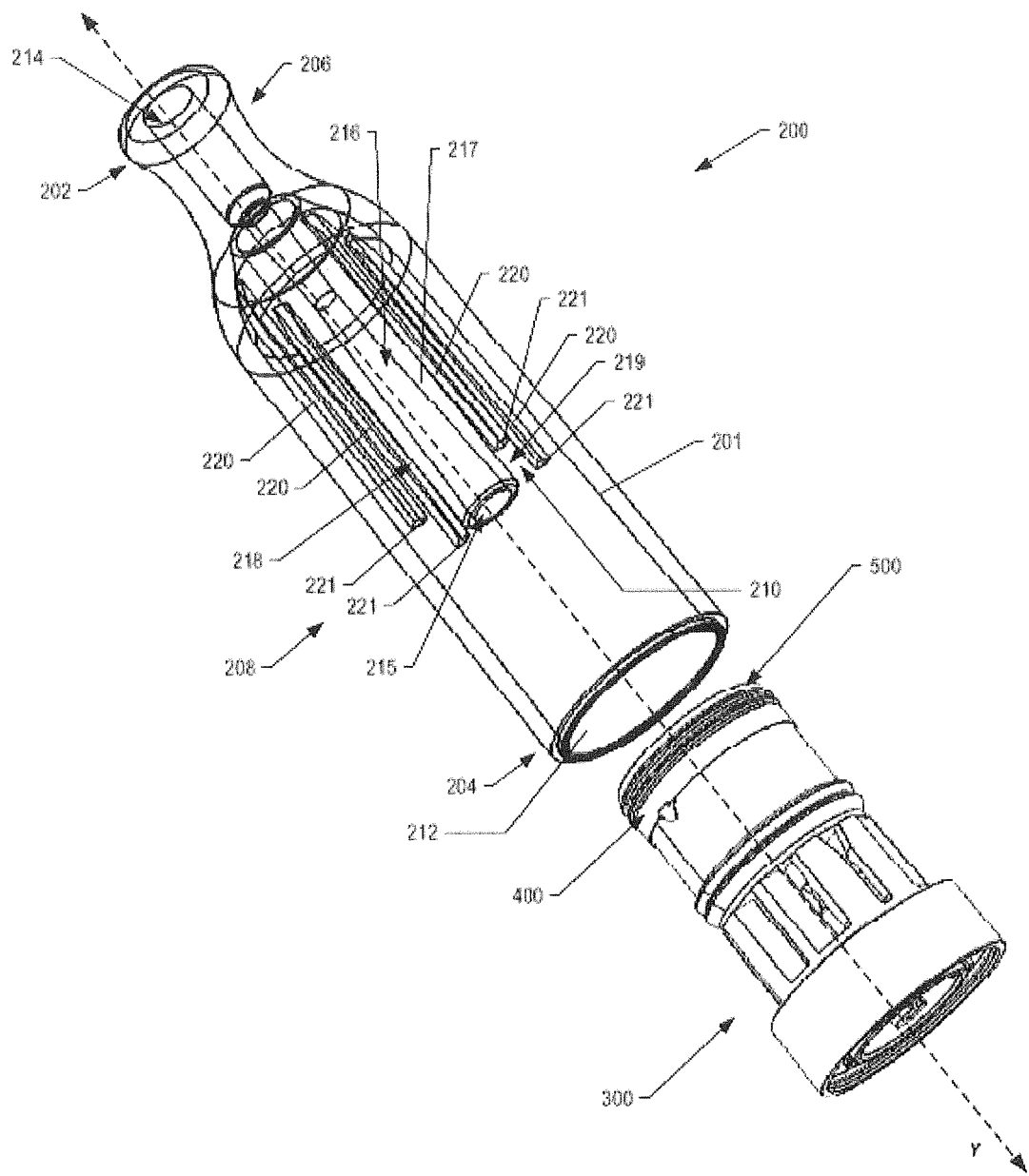
FIG. 3 is a partially exploded view of an aerosol delivery device with a reservoir housing shown as being transparent for convenience according to an example aspect of the present disclosure.
Figure 4:
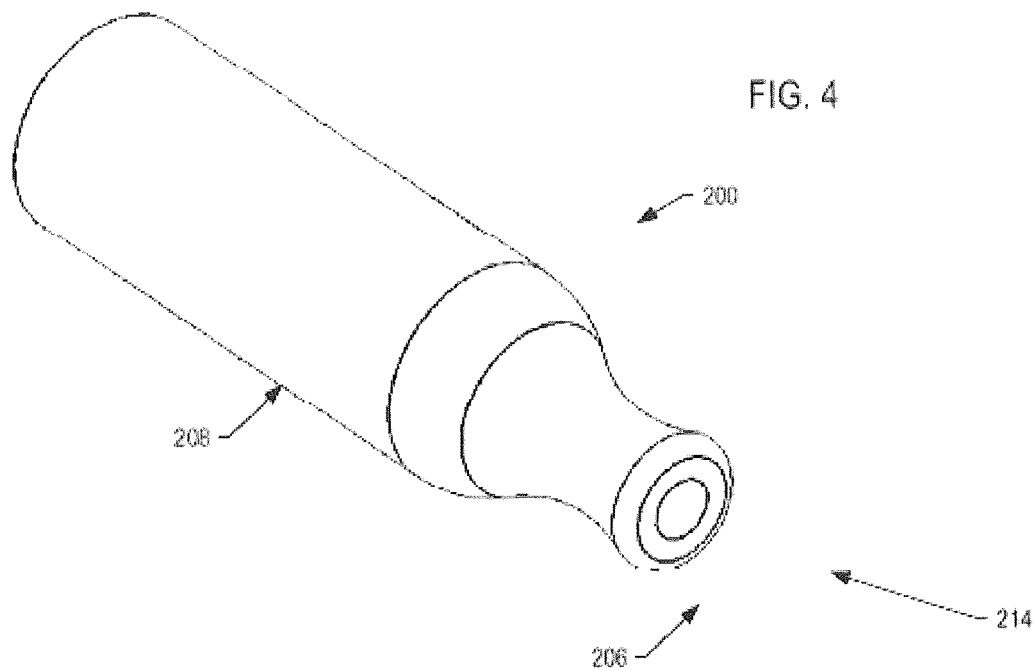
FIG. 4 is a perspective view of a reservoir housing according to an example aspect of the present disclosure.

Referring to FIG. 3, the reservoir housing 200 includes a first closed mouthend 202 and an opposing second connecting end 204. Additionally, the reservoir housing 200 includes an outer wall 201 that extends from the mouthend 202 to the connecting end 204 along a direction parallel to the longitudinal axis Y of the aerosol delivery device 10. In some aspects, the reservoir housing 200 may include a mouthpiece portion 206 disposed proximate the mouthend 202 of the reservoir housing 200 and a storage portion 208 that extends from the mouthpiece portion 206 towards the connecting end 204 of the reservoir housing 200. Additionally, the storage portion 208 may extend from the mouthpiece portion 206 towards the connecting end 204 along a direction parallel to the longitudinal axis Y of the aerosol delivery device 10. According to some aspects, the storage portion 208 may be configured to receive various components of the aerosol delivery device 10 within the outer wall 201 of the reservoir housing 200, as discussed in greater detail below.

In some aspects, the mouthpiece portion 206 disposed proximate the mouthend 202 of the reservoir housing 200 may include a tapered portion having a smaller diameter than other portions (e.g., storage portion 208) of the reservoir housing 200. According to some aspects, the aerosol delivery device 10 may include a mouthpiece channel 216 that is formed of an outer wall 217 disposed within the reservoir housing 200. For example, the mouthpiece channel 216 may be formed of an outer wall 217 that is substantially shaped as a cylindrical tube and is disposed interior to the outer wall 201 of the reservoir housing 200. Additionally, the mouthpiece channel 216 may include an opening 214 disposed proximate to the mouthend 202 of the reservoir housing 200. The opening 214 may provide for egress of formed aerosol from the aerosol delivery device 10. In particular, the mouthpiece channel 216 may be configured to be in fluid communication with the opening 214. Additionally, the mouthpiece channel 216 may include a second opening 215 disposed proximate a terminal end 219 of the mouthpiece channel 216. The second opening 215 may also be in fluid communication with the mouthpiece channel 216 and may also provide for egress of formed aerosol from the aerosol delivery device 10.

Figure 5:
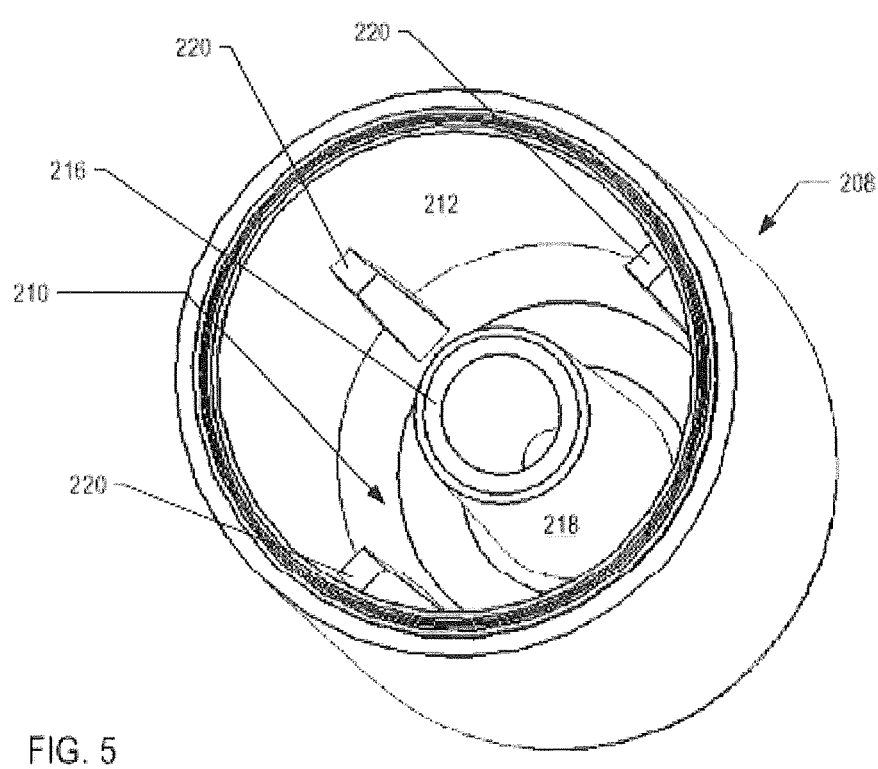
FIG. 5 is a perspective view of a reservoir housing and a reservoir chamber defined, in part, by the reservoir housing according to an example aspect of the present disclosure.
Figure 14A:
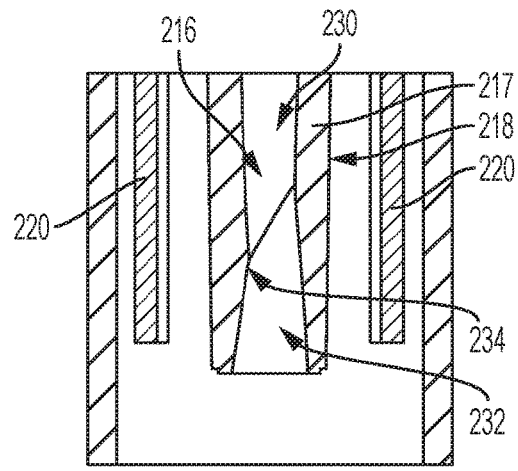
FIG. 14A is a sectional view of a portion of a reservoir housing according to an example aspect of the present disclosure.
Figure 14B:
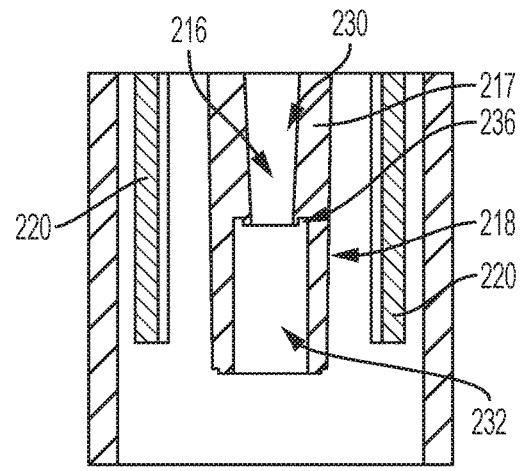
FIG. 14B is a sectional view of a portion of a reservoir housing according to an example aspect of the present disclosure.
Figure 14C:
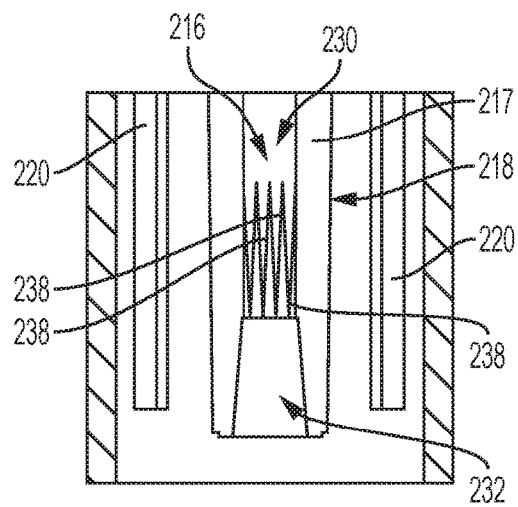
FIG. 14C is a sectional view of a portion of a reservoir housing according to an example aspect of the present disclosure.
Figure 14D:
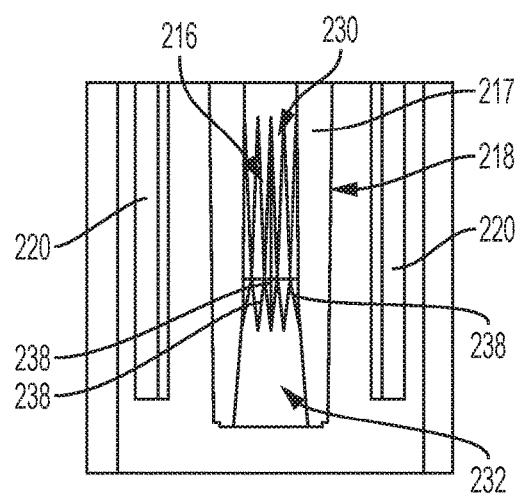
FIG. 14D is a sectional view of a portion of a reservoir housing according to an example aspect of the present disclosure.
Figure 15:
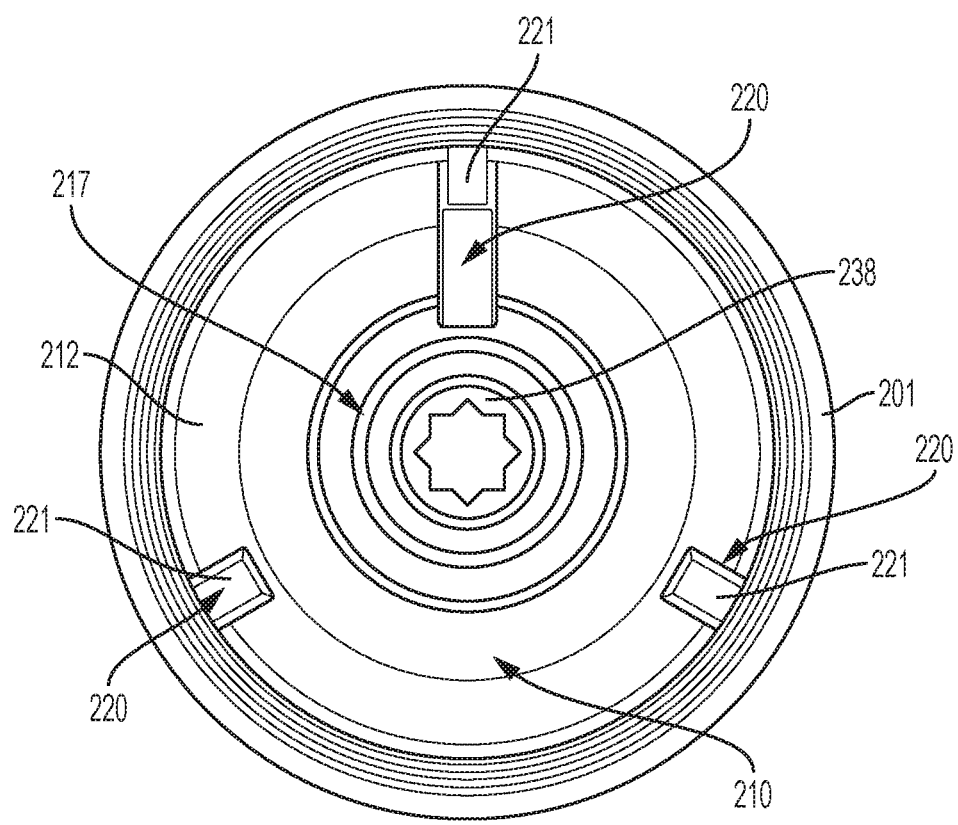
FIG. 15 is a bottom view of the reservoir housing shown in FIG. 14C according to an example aspect of the present disclosure.

As shown in FIGS. 3 and 5, the mouthpiece channel 216 may be substantially tubular and cylindrical in shape. Additionally, the mouthpiece channel 216 may extend from the mouthend 202 to the terminal end 219 of the mouthpiece channel 216. In some aspects, the mouthpiece channel 216 may extend from the mouthend 202 and towards the connecting end 204 of the reservoir housing 200 along a direction parallel to the longitudinal axis Y of the aerosol delivery device 10. In some aspects, the mouthpiece channel 216 may taper as it extends from a first end to a second end of the mouthpiece channel 216. According to some aspects, the mouthpiece channel 216 may be shaped and/or arranged so as to mitigate the likelihood of a meniscus forming within the mouthpiece channel 216. For example, as shown in FIG. 14A, the mouthpiece channel 216 may be shaped to include a first portion 230, a second portion 232, and a transition therebetween that includes an elliptical orifice 234. According to another aspect, as shown in FIG. 14B, the mouthpiece channel 216 may be shaped to include a first portion 230, a second portion 232, and a shoulder portion 236 disposed proximate therebetween that provides for a fluid trap configured to minimize the formation of condensation within the mouthpiece channel 216. In some aspects, as shown in FIGS. 14C and 14D, the mouthpiece channel 216 may include fluted elements 238 extending radially inward from the outer wall 217 that forms the mouthpiece channel 216. According to some aspects, as shown in FIG. 15, the fluted elements 238 may extend radially inward from the outer wall 217 so as to define a star-shaped radial cross-section of the mouthpiece channel 216 configured to prevent the formation of a meniscus therein. Additionally, the mouthpiece channel 216 may extend through a reservoir chamber 210 defined by the reservoir housing 200 and may be in fluid communication with the vaporizing assembly 300, as discussed in greater detail herein.

Referring to FIGS. 3 and 5, the storage portion 208 may define, in part, a reservoir chamber 210 configured to store an aerosol precursor composition therein. As previously mentioned, the reservoir housing 200 may be substantially tubular in shape, and more particularly, the storage portion 208 may be substantially tubular and/or cylindrically shaped. As shown in FIG. 5, the outer wall 201 that forms the substantially cylindrical tubular shaped reservoir housing 200 may include an interior surface 212. Additionally, the outer wall 217 that forms the mouthpiece channel 216 may include an exterior surface 218. The interior surface 212 of the outer wall 201 that forms the reservoir housing 200 and the exterior surface 218 of the outer wall 217 that forms the mouthpiece channel 216 may define, in part, the reservoir chamber 210 configured to retain an amount of aerosol precursor composition therein.

In some aspects, the reservoir housing 200 may further include at least one sealing member support 220. According to one aspect and as particularly shown in FIGS. 3 and 5, the reservoir housing 200 may include four sealing member support 220 arranged about the interior surface 212 of the outer wall 201 of the reservoir housing 200 in substantially equal angular intervals about the longitudinal axis Y of the aerosol delivery device 10. Although the reservoir housing 200 is shown as having four sealing member supports 220, one of ordinary skill in the art may appreciate that any number of sealing member supports are also encompassed by the present disclosure. In some aspects, the at least one sealing member support 220 may be integrally formed with the interior surface 212 of the outer wall 201. In another aspect, the sealing member support 220 may be securely affixed to the interior surface 212 of the reservoir housing 200.

Referring to FIGS. 3 and 5, the sealing member supports 220 may extend from proximate the mouthend 202 of the reservoir housing to a terminal end 221 along a direction substantially parallel to the longitudinal axis Y of the aerosol delivery device 10. In some aspects, the sealing member supports 220 may extend longitudinally along the interior surface 212 of the outer wall 201 of the reservoir housing 200. Further, the sealing member supports 220 may extend along a direction substantially parallel to the mouthpiece channel 216. According to some aspects, the mouthpiece channel 216 extends a greater distance along a direction substantially parallel to the longitudinal axis Y of the aerosol delivery device 10 than the distance any of the sealing member supports 220 extends along a direction substantially parallel to the longitudinal axis Y of the aerosol delivery device 10, as shown in FIG. 3. In particular, the terminal end 219 of the mouthpiece channel 216 extends beyond the terminal end 221 of the sealing member support 220 from the mouthend 202 of the reservoir housing 200.

As shown in FIGS. 3 and 5, the connecting end 204 of the reservoir housing 200 may be configured to receive a sealing member 500 therethrough. The sealing member 500 may be configured to directly engage the reservoir housing 200 so as to define the reservoir chamber 210 configured to retain the aerosol precursor composition therein. Additionally, the sealing member 500 may be in a sealing arrangement with the outer wall 201 of the reservoir housing 200 and the outer wall 217 of the mouthpiece channel 216 so as to define the reservoir chamber 210. In particular, the sealing member 500 may be configured to directly and sealingly engage the interior surface 212 of the storage portion 208 and the exterior surface 218 of the mouthpiece channel 216 such that the sealing member 500, the interior surface 212 of the storage portion 208, and the exterior surface 218 of the mouthpiece channel 216 define the reservoir chamber 210. Additionally, the sealing member supports 220 may be configured to directly engage the sealing member 500 when the sealing member 500 is disposed and/or received within the reservoir housing 200.

According to one aspect, the sealing member 500 may be configured to directly engage the interior surface 212 of the storage portion 208 so as to substantially prevent the aerosol precursor composition from traversing a circumferential peripheral surface 502 of the sealing member 500 that directly and sealingly engages the interior surface 212 of the storage portion 208. For example, the circumferential peripheral surface 502 of the sealing member 500 may further include at least one sealing element 504 that extends radially therefrom, as particularly shown in FIGS. 7A and 7B. The sealing element 504 may be configured to directly engage the interior surface 212 of the storage portion 208. In some aspects, the sealing element 504 may include a plurality of ridges, flanges, and/or the like that extend radially from and along the peripheral surface 502 of the sealing member 500 and are configured to directly and operably engage the interior surface 212 of the reservoir housing 200. When directly engaged with the interior surface 212, the sealing element 504 may be configured to substantially limit and/or prevent the aerosol precursor composition disposed within the reservoir chamber 210 from traversing the peripheral surface 502 of the sealing member 500 when the sealing member 500 is operably and directly engaged with the reservoir housing 200 and disposed therein.

Figure 7A:
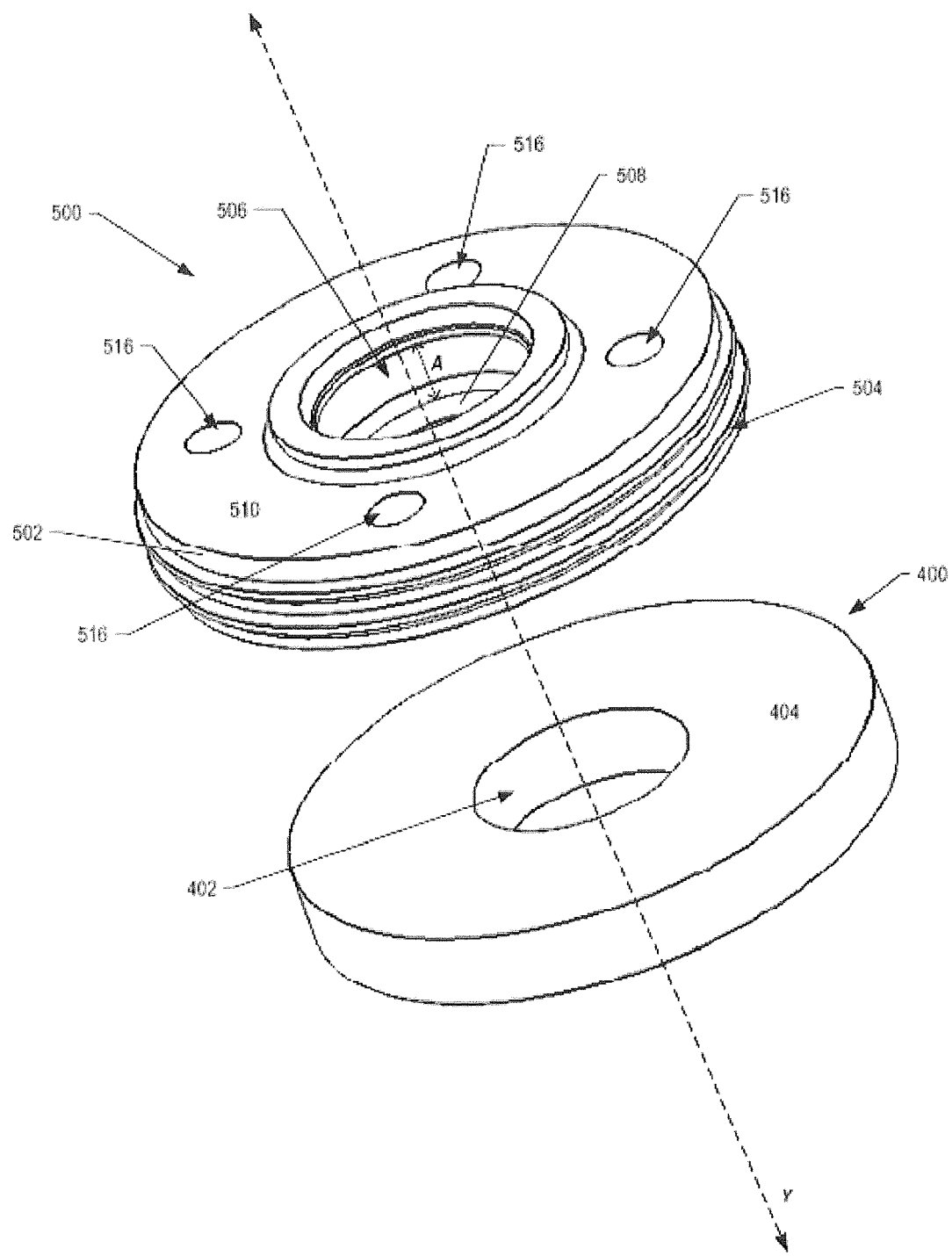
FIG. 7A is a top perspective view of a sealing member and a substrate member according to an example aspect of the present disclosure.
Figure 12:
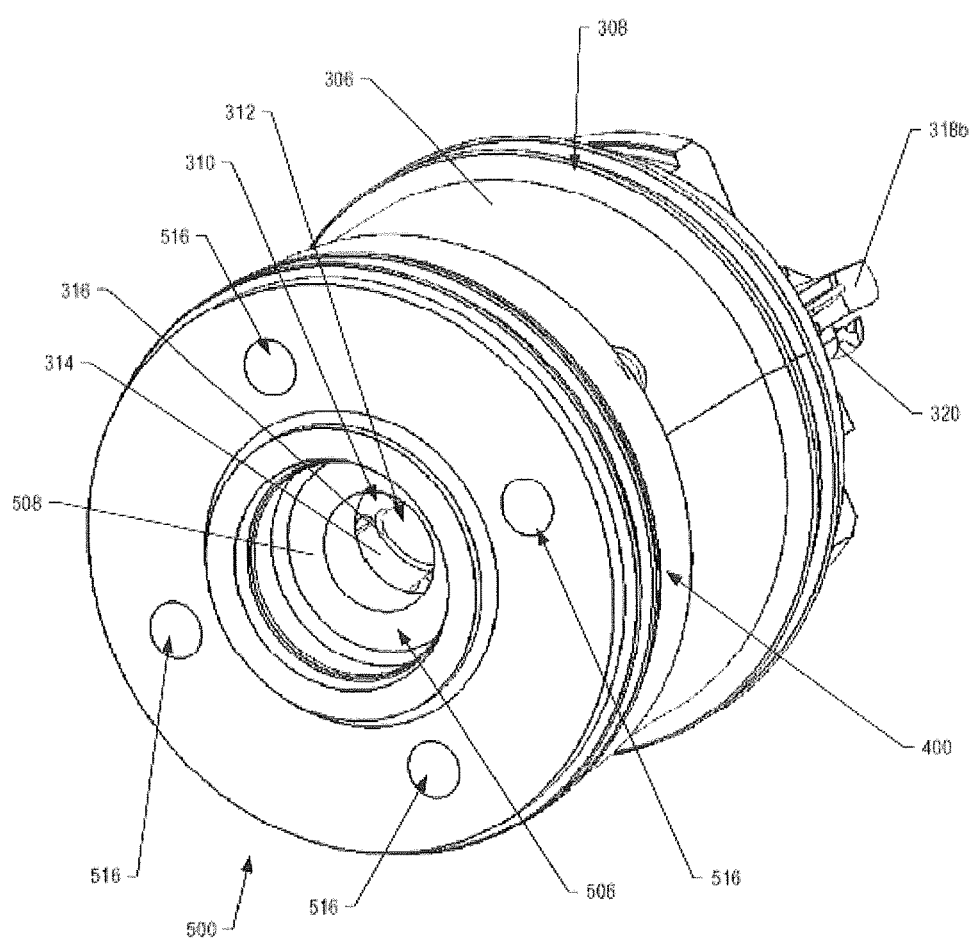
FIG. 12 is a perspective view of a vaporizing assembly operably engaged with a substrate member and a sealing member according to an example aspect of the present disclosure.

Additionally, the mouthpiece channel 216 may be configured to directly engage the sealing member 500 when the sealing member 500 is disposed and/or received within the reservoir housing 200. Referring to FIG. 7A, the sealing member 500 may define a sealing member vapor orifice 506 that extends therethrough. Additionally, the sealing member 500 may further include a flange portion 508 that may partially define a portion of the sealing member vapor orifice 506. For example, as shown in FIG. 12, the flange portion 508 may be shaped as an annular member that defines a medial portion of the sealing member vapor orifice 506. According to another aspect, the flange portion 508 may define a distal or proximal portion of the sealing member vapor orifice 506. Further, the portion of the sealing member vapor orifice 506 defined by the annular shaped flange portion 508 may have a smaller diameter than a diameter of at least another portion of the sealing member vapor orifice 506. Additionally, when the sealing member 500 is operably engaged with the reservoir housing 200 (e.g., the circumferential peripheral surface 502 is directly and sealingly engaged with an interior surface 212 of the reservoir housing, etc.), the annular shaped flange portion 508 may be configured to directly and sealingly engage the mouthpiece channel 216. In particular, the flange portion 508 provides a seat for the mouthpiece channel 216 to substantially abut such that the sealing member 500, the interior surface 212 of the reservoir housing 200, and the exterior surface 218 of the mouthpiece channel 216 enclose a volume that defines the reservoir chamber 210.

In some aspects, the sealing member vapor orifice 506 may be configured to provide for fluid communication between the mouthpiece channel 216 and the vaporizing assembly 300 when the mouthpiece channel 216 is disposed within the sealing member vapor orifice 506 and/or is substantially abutted against the flange portion 508 of the sealing member vapor orifice 506. For example, when the mouthpiece channel 216 substantially abuts the flange portion 508, the sealing member vapor orifice 506 may provide for fluid communication between the mouthpiece channel 216 and the vaporizing assembly 300 such that aerosol, vapor and/or the like formed by the vaporizing assembly 300 heating an aerosol precursor composition may egress the aerosol delivery device 10 via the opening 215 disposed proximate the terminal end 219 of the mouthpiece channel 216, the mouthpiece channel 216, and through the opening 214 disposed proximate the mouthend 202 of the reservoir housing 200. According to some aspects, when the mouthpiece channel 216 substantially abuts the flange portion 508 and/or is disposed within the sealing member vapor orifice 506, the operable engagement between the mouthpiece channel 216 and the sealing member vapor orifice 506 and/or the flange portion 508 may provide for an air-tight seal or a fluid-tight seal therebetween. The operable engagement between the mouthpiece channel 216 and the sealing member vapor orifice 506 and/or the flange portion 508 may advantageously prevent and/or substantially limit aerosol, vapor and/or the like formed by the vaporizing assembly 300 from entering the reservoir chamber 210. Additionally or alternatively, the operable engagement between the mouthpiece channel 216 and the sealing member vapor orifice 506 and/or the flange portion 508 may advantageously prevent and/or substantially limit the aerosol precursor composition retained within the reservoir chamber 210 from entering the mouthpiece channel 216, the sealing member vapor orifice 506, and/or the vaporizing assembly 300.

According to some aspects, the sealing member 500 may be further configured to directly engage at least one sealing member support 220 when the circumferential peripheral surface 502 of the sealing member 500 is directly engaged with an interior surface 212 of the reservoir housing 200 and/or when the sealing member vapor orifice 506 and/or the flange portion 508 of the sealing member 500 is directly engaged with the mouthpiece channel 216. In this regard, a first planar surface 510 of the sealing member 500 may be oriented, exposed, faced and/or the like towards the reservoir chamber 210 when the sealing member 500 is operably engaged with the reservoir housing 200. Additionally, when the sealing member 500 is operably engaged with the reservoir housing 200 and/or when the mouthpiece channel 210 is disposed within the sealing member vapor orifice 506 and/or substantially abutting the flange portion 508, the sealing member support 220 may substantially abut the first planar surface 510. In particular, the terminal end 221 of sealing member support 220 may substantially abut the first planar surface 510 of the sealing member 500 so as to prevent peripheral portions of the sealing member 500 from being displaced longitudinally towards the mouthend 202 of the reservoir housing 200. As shown in FIG. 7A, a longitudinal distance A exists between the flange portion 508 and the first planar surface 510 of the sealing member 500 such that the length of the distance A between the flange portion 508 and the first planar surface 510 of the sealing member 500 corresponds with the difference in length between the length of the mouthpiece channel 210 and the length of the sealing member support 220, as previously described herein.

Figure 6:
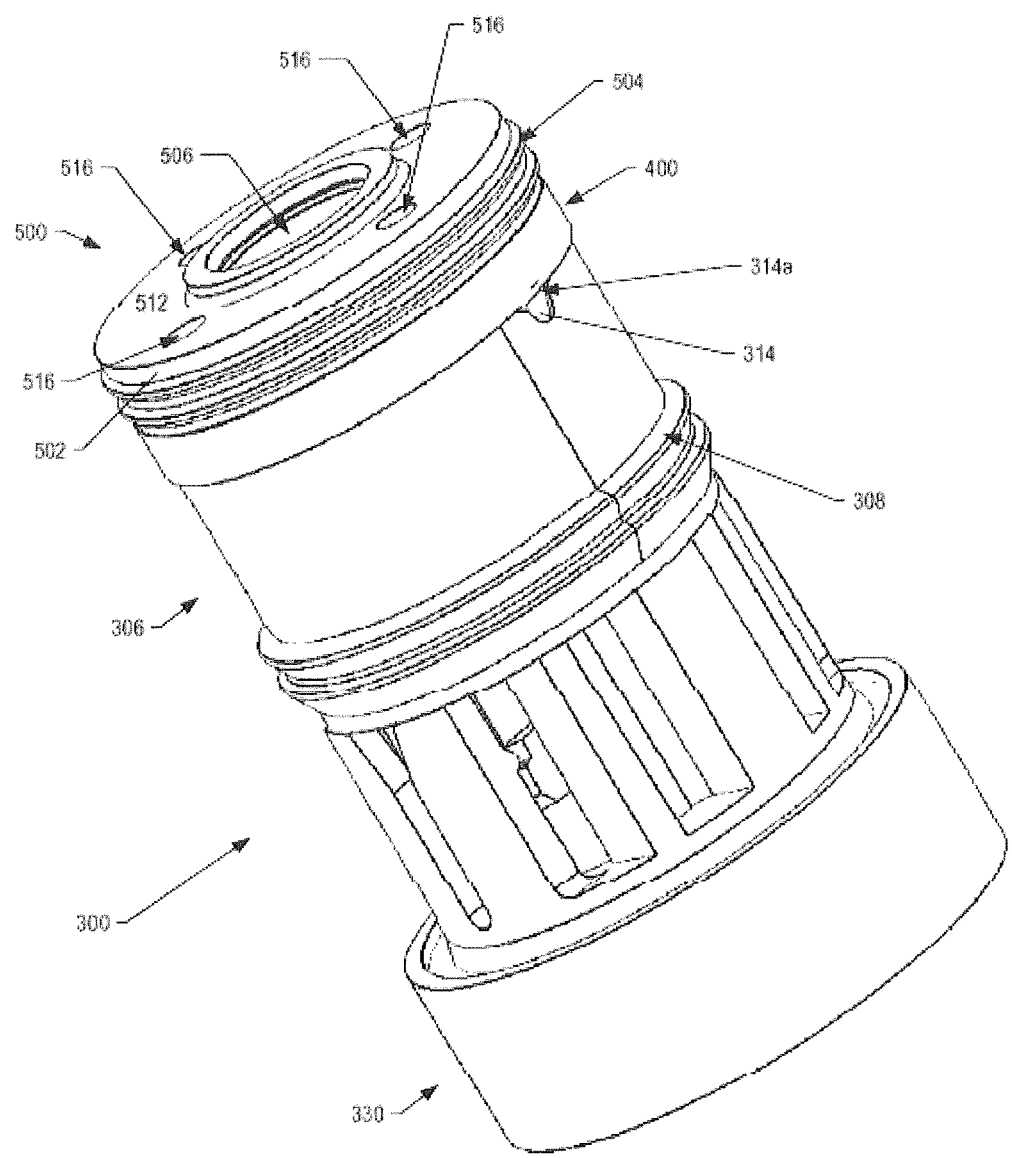
FIG. 6 is a perspective view of a sealing member, a substrate member, and a vaporizing assembly according to an example aspect of the present disclosure.
Figure 7B:
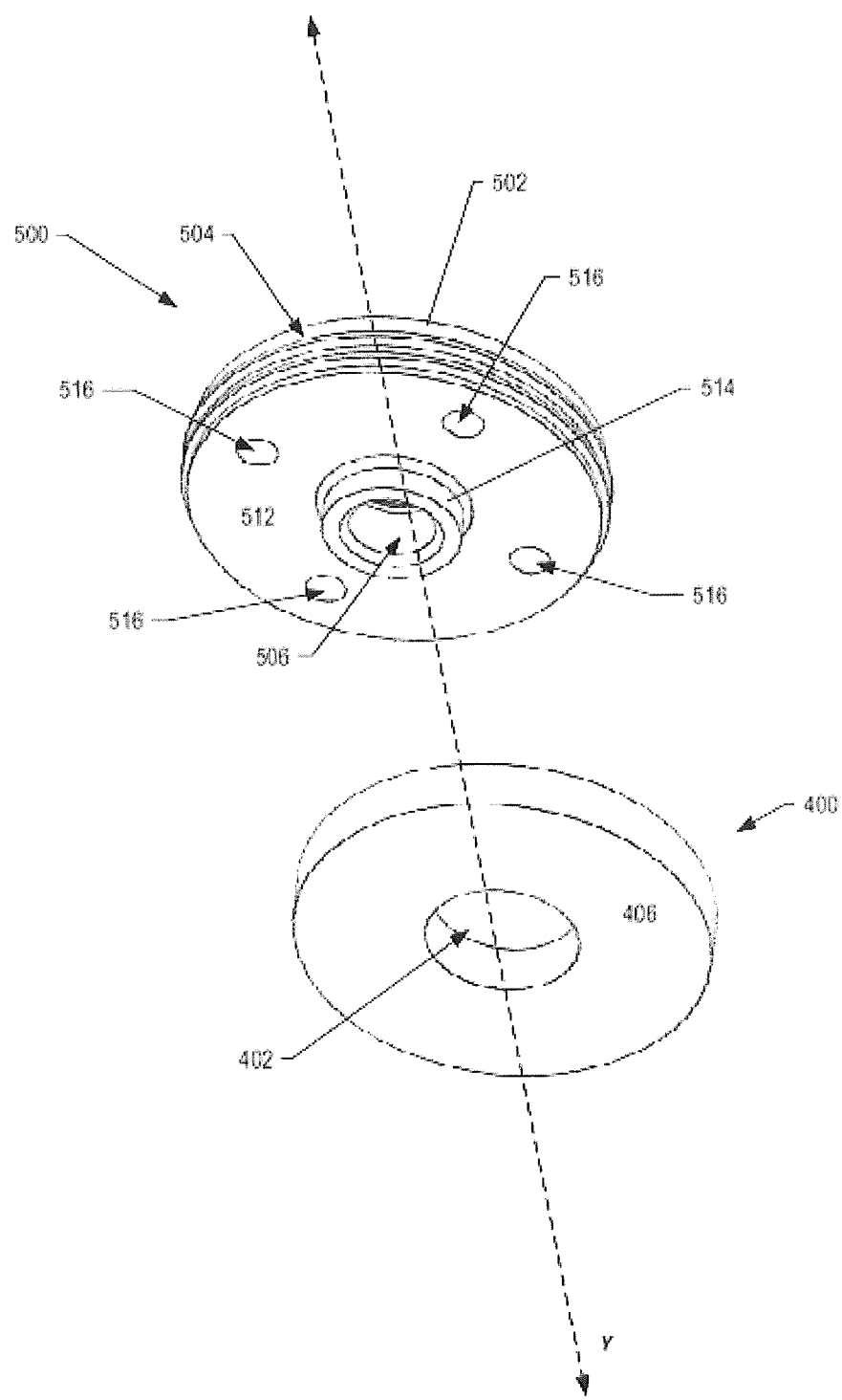
FIG. 7B is a bottom perspective view of a sealing member and a substrate member according to an example aspect of the present disclosure.

Referring to FIG. 7B, the sealing member 500 may further define a substrate engaging element 514 that extends along a direction parallel to the longitudinal axis Y of the aerosol delivery device 10. In particular, the substrate engaging element 514 may extend from a second planar surface 512, which is disposed opposite to the first planar surface 510 with respect to the longitudinal axis Y, of the sealing element 500. In some aspects, and as particularly shown in FIGS. 6 and 12, the sealing member 500 may be configured to operably engage the substrate member 400. For example, the substrate engaging element 514 may be configured to directly engage the substrate member 400 so as to limit the substrate member 400 from being displaced radially from the longitudinal axis Y of the aerosol delivery device 10 with respect to the sealing member 500. In particular, the substrate engaging element 514 may be disposed within a substrate member vapor orifice 402 that is defined by the substrate member 400. In some aspects, the substrate member vapor orifice 402 of the substrate member 400 may extend through the substrate member 400 completely, and a diameter of the substrate member vapor orifice 402 may be substantially consistent along the entire length of the substrate member vapor orifice 402. According to some aspects, the outermost diameter of the substrate engaging element 514 may be substantially equal to the diameter of the substrate member vapor orifice 402 such that when the substrate engaging element 514 is inserted therethrough, the substrate member 400 is prevented from being substantially displaced radially from the longitudinal axis Y with respect to the sealing member 500. Operable engagement between the substrate engaging element 514 of the sealing member 500 and the substrate member vapor orifice 402 may include a friction fit, press fit, interference fit, and/or the like such that radial displacement between the sealing member 500 and the substrate member 400 is substantially limited.

Additionally, the substrate member vapor orifice 402 may be configured to provide for fluid communication between any of the opening 214 of the mouthpiece channel 210 of the reservoir housing 200, the sealing member vapor orifice 506 of the sealing member 500, and the vaporizing assembly 300, such that aerosol, vapor and/or the like formed by the vaporizing assembly 300 heating an aerosol precursor composition may egress the aerosol delivery device 10 through the substrate member vapor orifice 402, the sealing member vapor orifice 506, the second opening 215 of the mouthpiece channel 216, the mouthpiece channel 216, and the opening 214 of the mouthpiece channel 216 disposed proximate the mouthend 202 of the reservoir housing 200.

As shown in FIGS. 6-7B, the sealing member 500 may further define at least one aerosol precursor composition orifice 516 that extends therethrough. In some aspects, the sealing member 500 may include four aerosol precursor composition orifices 516 that are arranged about the longitudinal axis Y of the aerosol delivery device 10 in substantially equal angular intervals. The at least one aerosol precursor composition orifice 516 is configured to provide for fluid communication between the reservoir chamber 210 and the substrate member 400. In particular, the substrate member 400 may include a first planar surface 404 that substantially abuts the second planar surface 512 of the sealing member 500 when the substrate engaging element 514 is directly engaged with the substrate member vapor orifice 402. Additionally, portions of the first planar surface 404 of the substrate member 400 may be exposed to respective aerosol precursor composition orifices 516 when the first planar surface 404 of the substrate member 400 substantially abuts the second planar surface 512 of the sealing member 500.

According to some aspects, the sealing member 500 may include any suitable number of aerosol precursor composition orifices 516 so as to provide for the precise transfer of a desired amount of aerosol precursor composition from the reservoir chamber 210 to the substrate member 400. Aerosol precursor composition orifices 516 may be shaped and/or configured so as to provide for the transfer of small volumes of liquid (i.e., an aerosol precursor composition and/or components thereof), such as milliliter or smaller, microliter or smaller, from the reservoir chamber 210 to the substrate member 400. Additionally and/or alternatively, an aerosol precursor composition orifice 516 may be shaped and/or configured so as to substantially limit and/or prevent any amount of aerosol precursor composition retained within the reservoir chamber 210 from vaporizing prematurely (i.e., vaporizing before being provided to the vaporizing assembly 300). For example, the aerosol precursor composition orifice 516 may be shaped and/or configured such that a pressure within the reservoir chamber 210 does not decrease past an operational threshold during use of the aerosol delivery device 10. In some aspects, the aerosol precursor composition orifice 516 may be approximately 0.047 mm. According to another aspect, the aerosol precursor composition orifice 516 may be about 0.065 mm. In yet another example aspect, the aerosol precursor composition orifice 516 may be about 0.080 mm. Additionally, the aerosol precursor composition orifice 516 may be sized in response to the surface energy of the aerosol precursor composition retained within the reservoir chamber 210. Such sizing can particularly be adapted to substantially resist bulk liquid flow from the reservoir chamber 210 until a negative pressure is applied (i.e., via a draw on the mouthend of the mouthend 202 of the device), at which time the desired volume of liquid may be expressed through the aerosol precursor composition orifice 516. Accordingly the aerosol precursor composition orifice(s) can have a size in the range of about 0.02 mm to about 0.11 mm, about 0.03 mm to about 0.1 mm, or about 0.04 mm to about 0.09 mm. When a plurality of aerosol precursor composition orifices is present, each orifice may have substantially the same size, or two or more orifices may have different sizes. Additionally or alternatively, another consideration when sizing the aerosol precursor composition orifice(s) 516 may include the density of the substrate, the amount of negative pressure within the aerosol delivery device during user operation, and/or the material selection of the sealing member 500. As such, the sealing member 500 may provide for the transfer of an aerosol precursor composition from the reservoir chamber 210 to the substrate member 400 in small, precise volumes and may provide for improving aerosol formation and/or reducing unnecessary power drain.

Figure 8:
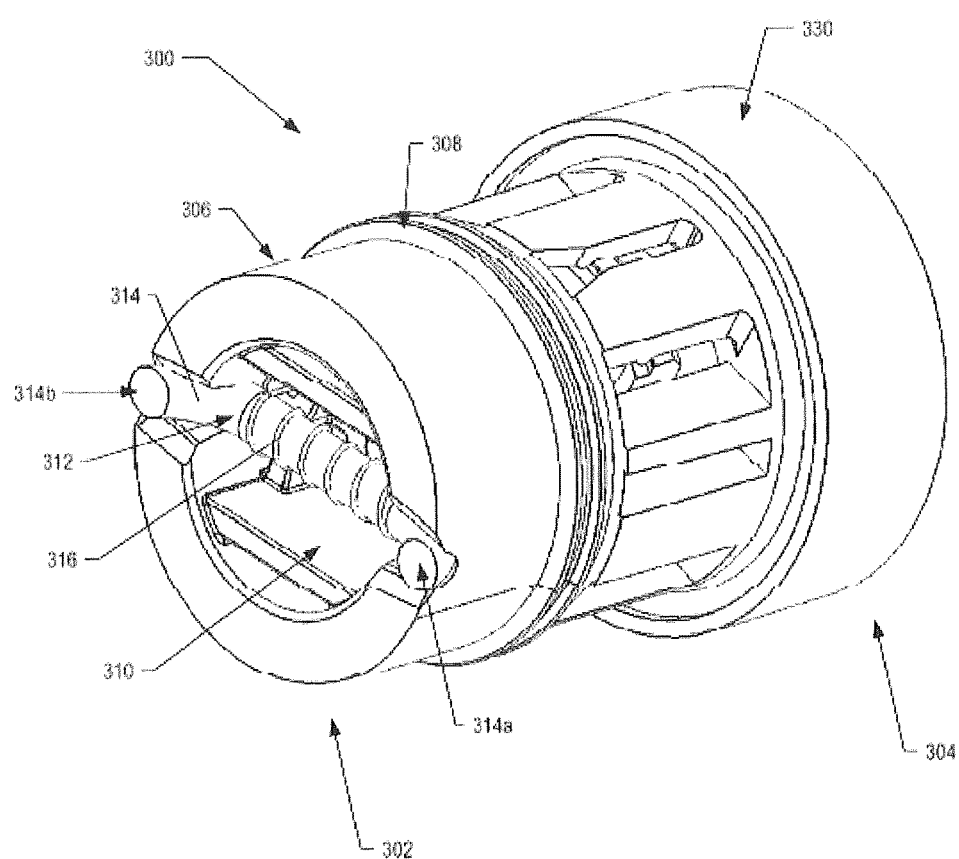
FIG. 8 is a perspective view of a proximal end of a vaporizing assembly according to an example aspect of the present disclosure.

Although FIGS. 3 and 5 illustrate the reservoir housing 200 defines a single reservoir chamber 210 when the sealing member 500 is disposed within and operably engaged with the reservoir housing 200, one of ordinary skill in the art may appreciate that an aerosol delivery device 10 may include a reservoir housing 200 defining any number of reservoir chambers 210. For example, in some aspects, a sealing member 500 defining four aerosol precursor composition orifices 516 may be operably engaged with a reservoir housing 200 that defines four distinct reservoir chambers 210 that are each compartmentalized and separated from one another. Particularly, each of the distinct reservoir chambers would be configured to fluidly communicate with a designated aerosol precursor composition orifice and would not be in fluid communication with any other reservoir chamber. In some aspects, components of an aerosol precursor composition may be separated and compartmentalized in distinct reservoir chambers and may be provided to the substrate member 400 in specific quantities based at least in part on the shape, configuration, and/or size of the specific aerosol precursor composition orifice 516 that is in fluid communication with the respective reservoir chamber.

Although the substrate member 400 is illustrated as being substantially annular in shape in FIGS. 7A and 7B, other suitable shapes (e.g., a rectangular ring, triangular ring or the like) and dimensions are also encompassed by the present disclosure. In some aspects, the substrate member 400 can have a relatively small thickness (e.g., about 1 mm to about 20 mm, about 1.5 to about 15 mm, or about 2 mm to about 10 mm). Additionally, FIGS. 7A and 7B illustrate that the first planar surface 404 of the substrate member 400 defines a surface area that is substantially equal to a surface area of an opposing second planar surface 406 of the substrate member 400. Although FIGS. 7A and 7B illustrate the surface area of the first planar surface 404 and the surface area of second planar surface 406 of the substrate member 400 are substantially equal to one another, one of ordinary skill in the art may appreciate that the respective surface areas of the first and second planar surfaces 404, 406 may differ in magnitude from one another. According to some aspects, the substrate member 400 defines a surface area of the first and second planar surfaces 404, 406, which are both about 0.5 $cm^2$ to about 50 $cm^2$, about 1 $cm^2$ to about 45 $cm^2$, about 2 $cm^2$ to about 40 $cm^2$, or about 3 $cm^2$ to about 30 $cm^2$.

The substrate member 400 can be formed of any material that is sufficiently and/or substantially inert with respect to the aerosol precursor composition and with respect to the amount of heating required for the vaporization of the aerosol precursor composition. In particular, the substrate member 400 is preferably chemically non-reactive with the components of the aerosol precursor composition (including aerosol forming materials, flavoring materials, and the like). Additionally, the substrate member 400 is preferably thermally and mechanically stable under the conditions of use. For example, the substrate member 400 may be formed of a material that is temperatures stable at a temperature of about 100° C. or greater, about 150° C. or greater, about 200° C. or greater, about 300° C. or greater, about 400° C. or greater, or about 500° C. or greater. In some aspects, the substrate member 400 may include a plurality of layers of nonwoven fibers. For example, the substrate member 400 may include cellulose acetate (CA) fibers, polyethylene terephthalate (PET) bicomponent fibers, polyvinyl alcohol (PVOH) fibers, and/or the like. Other materials, such as fiberglass fibers, are also encompassed by the present disclosure. Additionally or alternatively, the substrate member 400 may include fiberglass fibers, a porous ceramic material, particularly a silicon-based material, a silicon nitride material, and/or a porous glass or quartz material. Further, certain thermoplastic materials, such as cyclic olefin copolymers (COC) can be incorporated within the substrate member 400. Additionally and/or alternatively, the substrate member 400 may include wicking and/or porous materials that provide for the movement of the aerosol precursor composition therethrough (e.g., via capillary action), such that the aerosol precursor composition may be drawn to a liquid transport element 314, as described in greater detail herein. The substrate member 400 may include any combination of materials to provide for capillary action so as to provide the liquid transport element 314 an amount of aerosol precursor composition, as described in U.S. patent application Ser. No. 14/989,109, filed Jan. 5, 2016, which is incorporated by reference herein in its entirety.

Referring to FIG. 8, the vaporizing assembly 300 configured to be at least partially received within the reservoir housing 200 may include an atomizer housing 306 and a connector housing 330 operably engaged therewith. In particular, the atomizer housing 306 may be disposed proximate a vaporizing end 302 of the vaporizing assembly 300, and the connector housing 300 may be disposed proximate an opposed connecting end 304 of the vaporizing assembly 300. According to some aspects, the atomizer housing 306 may be operably engaged with the connector housing 330 in a friction fit, interference fit, magnetic fit, snap fit and/or the like. In some aspects, the atomizer housing 306 and the connector housing 330 may be securely affixed and/or attached to one another through ultrasonic welding and/or the like. Although the atomizer housing 306 and the connector housing 330 are illustrated as being separate members, the atomizer housing 306 and the connector housing 330 may be integrally formed with one another.

The atomizer housing 306 and/or the connector housing 330 may be sized and/or shaped such that the atomizer housing 306 and/or at least a portion of the connector housing 330 are disposed within the reservoir housing 200, as shown in FIG. 1. In some aspects, the atomizer housing 306 may include a plurality of sealing elements 308 configured to directly engage an interior surface 212 of the reservoir housing 200. In some aspects, the sealing element 308 may include a plurality of ridges, flanges, and/or the like that extend circumferentially about a peripheral surface of the atomizer housing 306. In particular, the sealing elements 308 may be configured to substantially limit and/or prevent the aerosol precursor composition and/or any aerosol formed within a vaporizing chamber 310 from traversing the sealing elements 308 disposed on the peripheral surface of the atomizer housing 306 and escape the aerosol delivery device 10 via means other than the mouthpiece channel 216 and/or the openings 214, 215 of the mouthpiece channel 216.

Additionally, the aerosol delivery device 10 includes an atomizer 312 disposed within the vaporizing chamber 310. The atomizer 312 includes an liquid transport element 314 that includes a first end 314*a* and a second end 314*b*. When the vaporizing assembly 300 is operably engaged with the substrate member 400, and more particularly, when the vaporizing end 302 of the vaporizing assembly 300 substantially abuts the substrate member 400, as shown in FIGS. 6, 9, and 12, each of the first and second ends 314*a*, 314*b* of the liquid transport element 314 directly engage the substrate member 400. For example, the first and second ends 314*a*, 314*b* of the liquid transport element 314 may substantially abut a portion of the second planar surface 406 of the substrate member 400 such that the liquid transport element 314 is in fluid communication with the substrate member 400. Additionally, a medial portion of the liquid transport element 314 extends between the first end 314*a* and the second end 314*b* and may include wicking and/or porous materials that provide for the movement of the aerosol precursor composition therethrough (e.g., via capillary action), such that the aerosol precursor composition may be drawn proximate to a heating element 316.

Additionally or alternatively, the substrate member 400 may define at least one orifice configured to receive at least a portion of the liquid transport element 314 proximate the first and second ends 314*a*, 314*b* therethrough. For example, the substrate member 400 may define an orifice sized similarly to an aerosol precursor composition orifice 516 defined by the sealing member 500, and the orifice defined by the substrate member 400 may be aligned with the aerosol precursor composition orifice 516 of the sealing member 500. In some aspects, a portion of the liquid transport element 314 proximate the first and second ends 314a, 314b may extend though the orifice defined by the substrate member 400 and the aligned aerosol precursor composition orifice 516 of the sealing member 500 so as to be in direct fluid communication with the aerosol precursor composition within the reservoir chamber 210. According to some aspects, the first and second ends 314a, 314b extending through the aerosol precursor composition orifices 516 may provide for the movement of the aerosol precursor composition within the reservoir chamber 210 (e.g., via capillary action), such that the aerosol precursor composition is drawn proximate to the heating element 316. In another aspect, the remaining aerosol precursor composition orifices 516 not engaged with the first and second ends 314a, 314b of the liquid transport element 314 may be engaged with the substrate member 400 so as to retain the aerosol precursor composition within the reservoir chamber 210 and/or to provide for the precise transfer of a desired amount of aerosol precursor composition from the reservoir chamber 210 to the substrate member 400. As shown in FIG. 8, the heating element 316 may be in a heating arrangement with the liquid transport element 314. In particular, the heating element 316 may extend at least partially about the medial portion of the liquid transport element 314, and more particularly, may extend at least partially about the liquid transport element 314 at a position between the first end 314a and the second end 314b of the liquid transport element 314. In some aspects, the heating element 316 may be configured to heat the aerosol precursor composition disposed within the medial portion of the liquid transport element 314 to produce an aerosol for inhalation by a user. In particular, the heating element 316 may be formed from a material that provides resistive heating when an electrical current is applied thereto.

Figure 11:
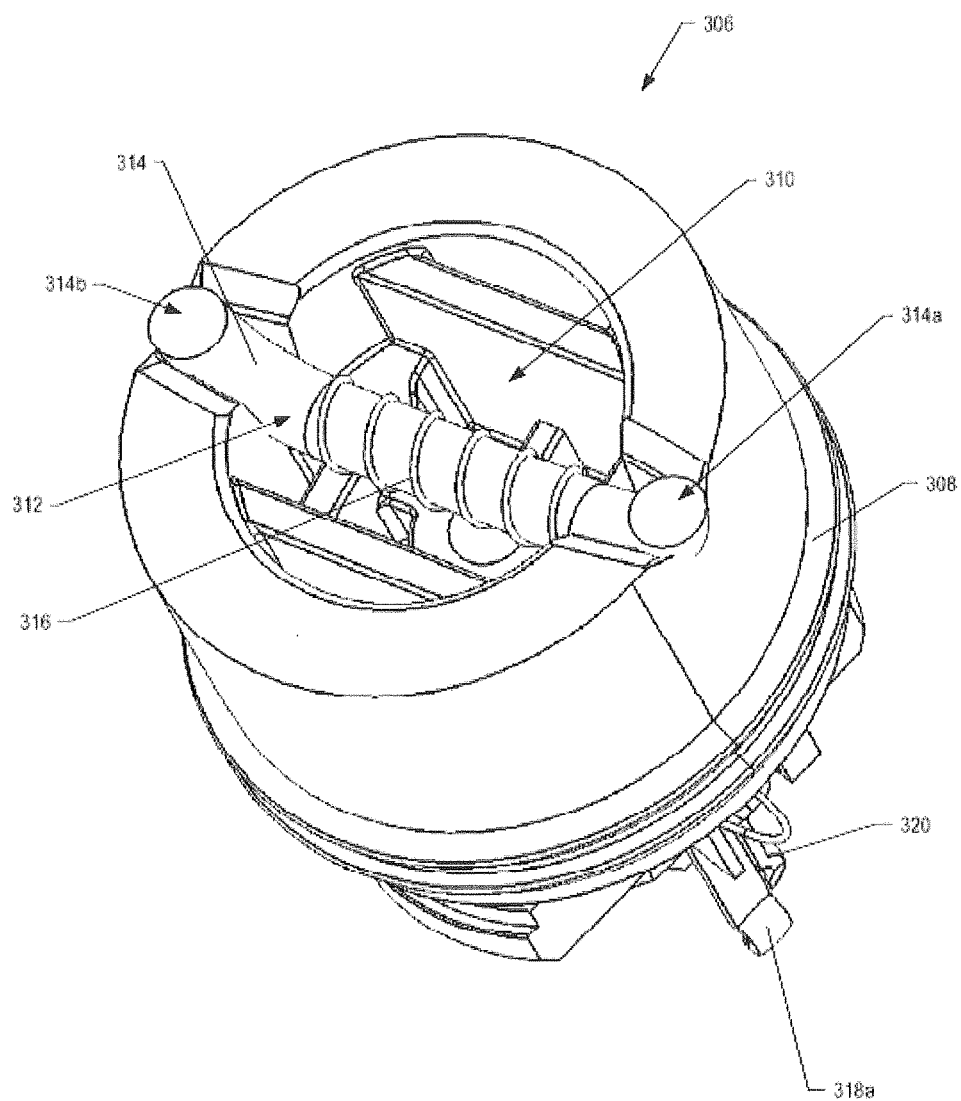
FIG. 11 is a perspective view of a vaporizing assembly having a connector housing (shown removed from the vaporizing assembly for clarity of view) according to an example aspect of the present disclosure.

As shown in FIGS. 8 and 11, the resistive heating element 316 may include a wire defining a plurality of coils wound about the medial portion of the liquid transport element 314. Additionally, as shown in FIGS. 8-11, the heating element 316 may include a wire material that provides resistive heating and may extend between a first electrical terminal 318a and a second electrical terminal 318b. For example, the wire material may include Kanthal (FeCrAl), Nichrome, Molybdenum disilicide ($MoSi_2$), Molybdenum disilicide doped with Aluminum ($Mo(Si,Al)_2$), ceramics (e.g., a positive temperature coefficient ceramic), titanium and/or related alloys in some aspects, although various other materials may be employed in other aspects. According to some aspects, the heating element 316 may be formed by winding the wire about the liquid transport element 314 as described in U.S. Pat. No. 9,210,738 to Ward et al., which is incorporated herein by reference in its entirety. However, various other aspects of methods may be employed to form the heating element 316, and various other aspects of heating element may be employed in the atomizer 312. For example, the heating element 316 may be configured to heat the aerosol precursor composition disposed within the liquid transport element 314 via radiant heating, as described in U.S. patent application Ser. No. 14/808,405, filed Jul. 24, 2015; Ser. No. 14/958,651, filed Dec. 3, 2015, the contents of which are incorporated herein in their entirety by reference. In another aspect, the heating element 316 may be configured to heat the aerosol precursor composition via inductive heating, as described in U.S. patent application Ser. No. 14/958,651, filed Dec. 3, 2015; Ser. No. 14/934,763, filed Nov. 6, 2015, the contents of which are incorporated herein in their entirety by reference.

In some aspects, the first electrical terminal 318a and a second electrical terminal 318b may be configured to provide the resistive heating element 316 with an electrical current when the vaporizing assembly 300 is operably engaged with a power source assembly 600. In some aspects, the heating element 316 may be integrally formed with the first and second electrical terminals 318a, 318b. In another aspect, the heating element 316 may be operably engaged with and in electrical communication with the first and second electrical terminals 318a, 318b. For example, portions of the heating element 316 may be welded, soldered, brazed, and/or the like to the respective first and second electrical terminals 318a, 318b. In some aspects, the first and second electrical terminals 318a, 318b may operably engage the power source disposed within the power source assembly 600 with the first and second electrical terminal tabs 319a, 319b. For example, in some aspects a circuit may be completed when the first and second electrical tabs 319a, 319b are operably engaged with the power source disposed in the power source assembly 600. The power source may provide an electrical current through the heating element 316 when the first and second electrical tabs 319a, 319b complete the electrical circuit and are engaged with the first and second electrical terminals 318a, 318b. The aerosol precursor composition disposed within the medial portion of the liquid transport element 314 is heated by the wire coils of the heating element 316 wound about the medial portion of the transport element 314. Although the heating element 316 is illustrated as a wire having a plurality of coils wound about the aerosol precursor transport element 314, additional forms for the heating element 316 are also encompassed by this disclosure, such as a heating element in the form of a foil, a foam, discs, spirals, fibers, wires, films, yarns, strips, ribbons, and/or cylinders.

Additionally, the first and second electrical terminals 318a, 318b may be configured to provide an electrical current to the heating element 316 when a control component of the aerosol delivery device 10, which may be disposed within the vaporizing assembly 300, the reservoir housing 200, and/or the power source assembly 600, actuates electrical current flow from the power source to the heating element 316 via the first and second electrical terminals 318a, 318b. In particular, the aerosol delivery device 10 may include a control component (i.e., a controller) 322 configured to at least control the heating of the heating element 316 and/or other operations of the aerosol delivery device 10 (e.g., powering and/or actuating various visual indicia and/or the like).

For example, the vaporizing assembly 300 may include a control component 322 and at least one control component terminal 320. In some aspects, the aerosol delivery device 10 may include a control component 322 as described in U.S. Pat. App. Pub. No. 2015/0245658 to Worm et al., which is incorporated herein by reference in its entirety. The control component terminal 320 may be configured to operably engage the power source (not shown) disposed in the power source assembly 600 when the connector housing 330 is directly and/or mechanically engaged with the power source assembly 600. In particular, the control component terminal 320 may be operably engaged with the power source so as to provide an electrical current to power the control component 322 to control the various operations of the aerosol delivery device 10. According to some aspects, the control component terminal 320 may be configured to receive electrical signals from additional and/or alternative control components (e.g., a separate control component, etc.) disposed within the power source assembly 600. Additionally, the control component terminal 320 may be configured to provide for electrical communication (i.e., electrical current, data signals, and/or the like) between a control component disposed within the power source assembly 600 and the control component 322 disposed within the vaporizing assembly 300. Additionally or alternatively, the power source assembly 600 may include a single control component (not shown) therein that is configured to control various operations of the aerosol delivery device 10, as previously described herein. For example, the power source assembly 600 may include a housing configured to store a control component and/or a control component terminal therein, as described in U.S. Pat. App. Pub. No. 2015/0335071 to Brinkley et. al, which is incorporated herein by reference in its entirety.

Figure 9:
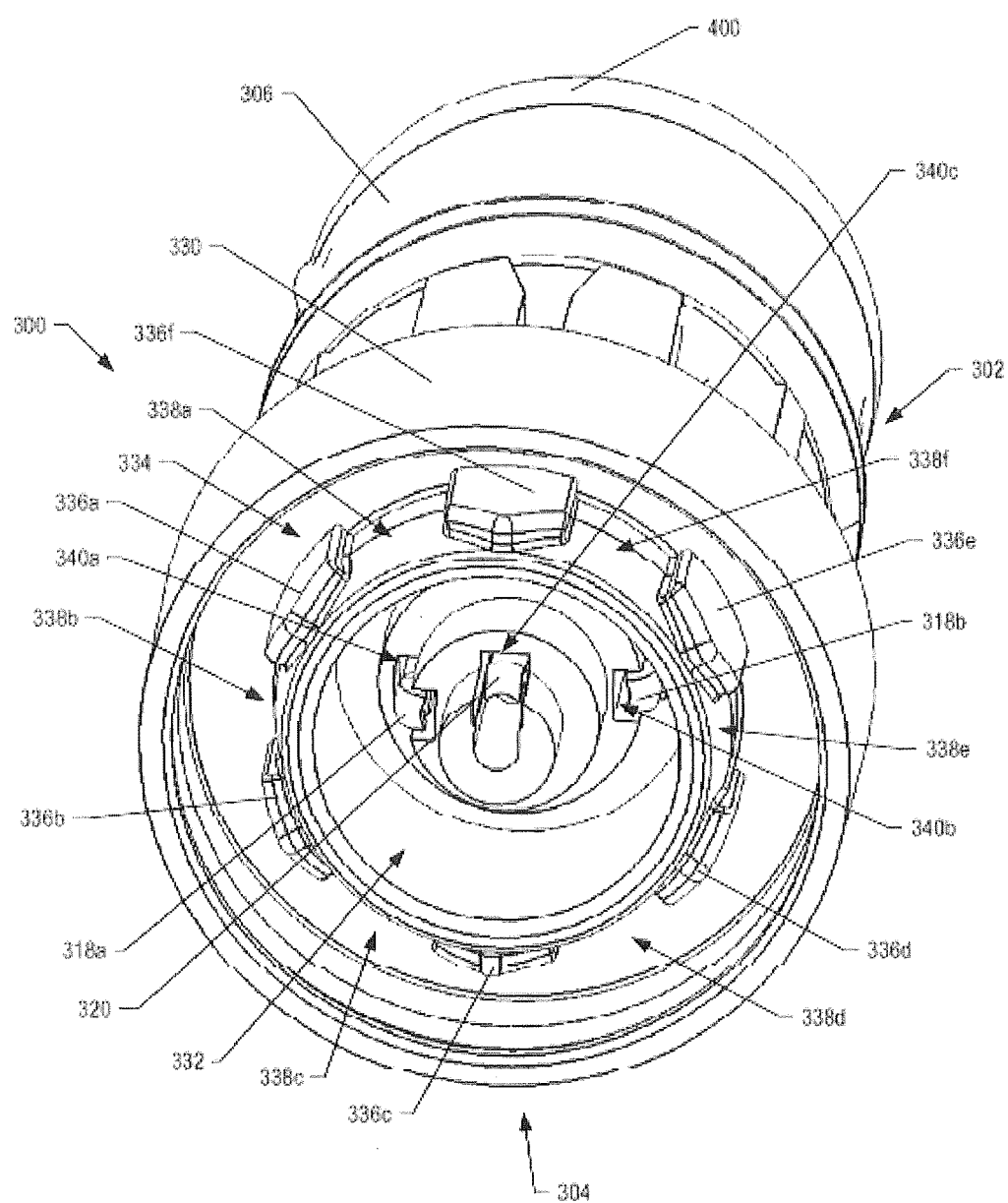
FIG. 9 is a perspective view of a distal end of a vaporizing assembly according to an example aspect of the present disclosure.
Figure 10:
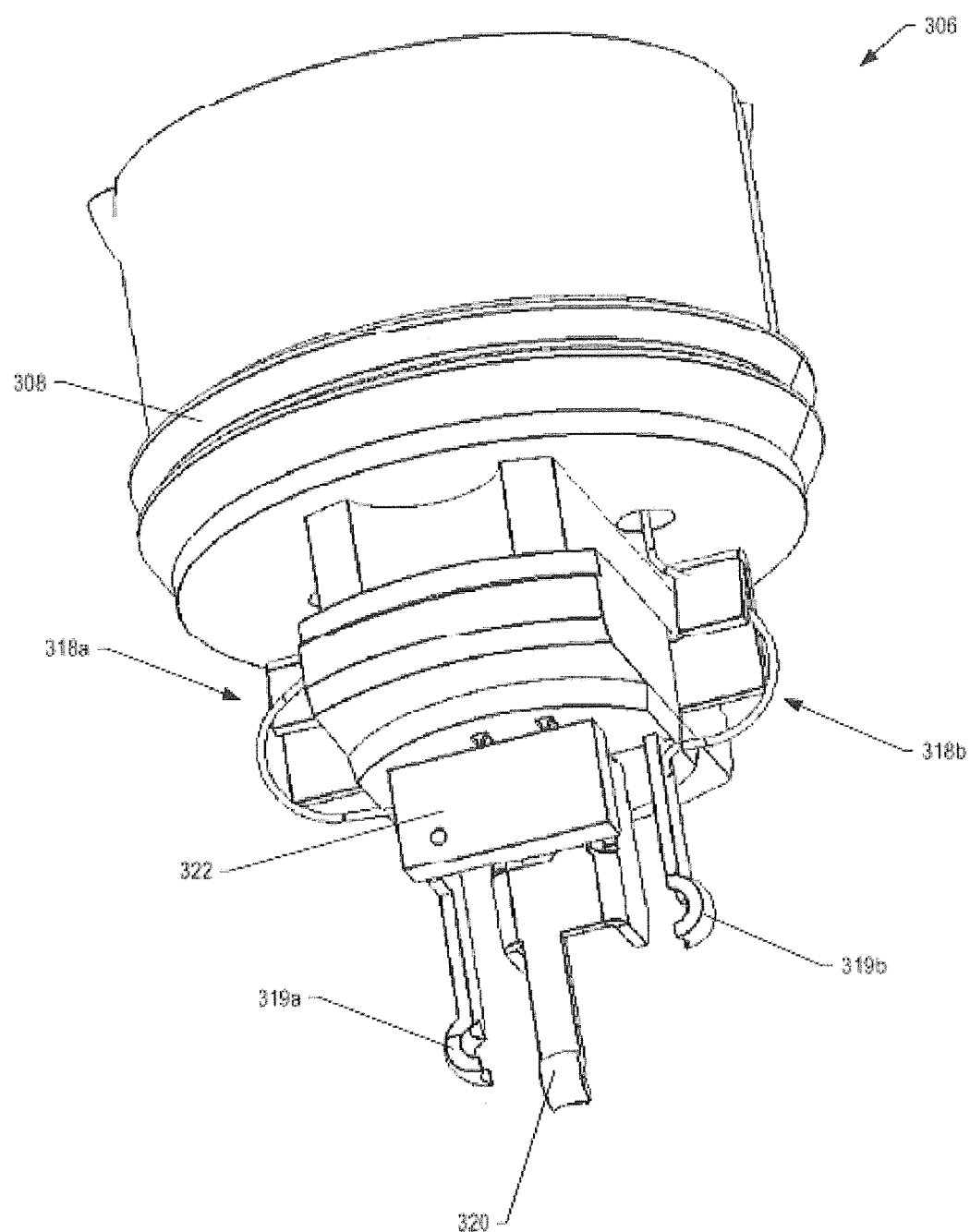
FIG. 10 is a perspective view of a vaporizing assembly having a connector housing (shown removed from the vaporizing assembly for clarity of view) according to an example aspect of the present disclosure.

Referring to FIG. 9, the connector housing 330 of the vaporizing assembly 300 may be configured to operably and/or mechanically engage the power source assembly 600. In some aspects, the connector housing 330 may be configured to receive at least a portion of the power source assembly 600 therein. Additionally, the connector housing 330 may be configured to provide access to at least one of the first electrical terminal 318a, the second electrical terminal 318b, and/or the control component terminal 320. For example, the connector housing 330 may include a coupler 332 configured to directly and mechanically engage at least a portion of the power source assembly 600.

Additionally, the coupler 332 may define a plurality of apertures 340a, 340b, 340c configured to receive the first electrical terminal 318a, the second electrical terminal 318b, and the control component terminal 320 therethrough respectively. Further, the coupler 332 may be particularly shaped and/or configured such that the connector housing 330 may only mechanically engage an authentic power source assembly 600. In particular, an authentic power source assembly 600 may be reciprocally shaped with respect to the coupler 332 such that the appropriate engagement between the power source assembly 600 and the connector housing 330 may only be accomplished when authentic power source assemblies 600 are engaged with authentic connector housings 330. For example, an authentic connector housing 330 may include a coupler 332 disposed proximate the connecting end 304 of the vaporizing assembly 300.

According to some aspects, the coupler 332 may provide benefits in terms of ease of assembly and easy of attachment to the power source assembly 600. In some aspects, the coupler 332 may be particularly shaped such that the reciprocally shaped power source assembly 600 may only mechanically engage the coupler 332 when the components are particularly aligned with respect to one another (i.e., axially and rotationally aligned with one another). For example, the coupler 332 may include an anti-rotation mechanism 334 configured to prevent rotation of the vaporizing assembly 300 with respect to the power source assembly 600 when engaged therewith. In some aspects where the reservoir housing 200 is securely attached and/or affixed to the vaporizing assembly 300 (e.g., ultrasonically welded), the anti-rotation mechanism 334 may be configured to prevent rotation of the reservoir housing 200 with respect to the power source assembly 600 when the connector housing 330 is mechanically engaged with the power source assembly 600. Such anti-rotation mechanisms are described in greater detail in U.S. Pat. App. Pub. No. 2014/0261495 to Novak III, et al., which is incorporated herein in its entirety by reference.

In some aspects, the anti-rotation mechanism 334 may include a plurality of protrusions 336a, 336b, 336c, 336d, 336e, 336f and a plurality of recesses 338a, 338b, 338c, 338d, 338e, 338f disposed about an outer periphery of a coupler 332 in an alternating arrangement. The power source assembly 600 may include a reciprocal arrangement (not shown) of a plurality of recesses and a plurality of protrusions configured to directly engage the plurality of protrusions 336a, 336b, 336c, 336d, 336e, 336f and the plurality of recesses 338a, 338b, 338c, 338d, 338e, 338f alternatingly disposed about the outer periphery of the coupler 332. According to some aspects, the anti-rotation mechanism 334 of the connector housing 330 may advantageously provide for ease of alignment and reliable engagement with the power source assembly 600 when operably and directly engaged therewith. For example, the anti-rotation mechanism 334 may provide for alignment of the connector housing 330 with the power source assembly 600 such that the first and second heating terminals 318a, 318b and/or the control component terminal 320 are aligned with respective terminals, connectors, and/or the like disposed within the power source assembly 600 when the connector housing 330 is engaged therewith. Further, the anti-rotation mechanism 334 may substantially limit any rotation of the connector housing 330 with respect to the power source assembly 600 when the connector housing 330 and the power source assembly 600 are mechanically engaged therewith. In some embodiments, the connector housing 330 may include additional engagement assemblies that provide for a threaded fit, friction fit, interference fit, magnetic fit, and/or the like with the power source assembly 600.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. No. 9,220,302 to DePiano et al.; U.S. Pat. App. Pub. Nos. 2010/0163063 by Fernando et al.; 2013/0192623 to Tucker et al.; 2013/0298905 to Leven et al.; 2013/0180553 to Kim et al. and 2014/0000638 to Sebastian et al.; 2014/0261495 to Novak et al.; which are incorporated herein by reference.

Referring to FIG. 13, aspects of the present disclosure may provide for a method 1300 of manufacturing a liquid storage tank for an aerosol delivery device. The method 1300 may include providing a reservoir chamber 1302 defined, in part, by an outer housing formed of a wall and a central tube interior to the outer housing and formed of a wall. For example, the reservoir chamber 210 may be defined, in part, by the interior surface 212 of the outer wall 201 that forms the reservoir housing 200 and the exterior surface 218 of the outer wall 217 that forms the mouthpiece channel 216. The outer housing (e.g., the reservoir housing 200) may include a closed mouthend and an opposing connecting end, and the central tube (e.g., the mouthpiece channel 216) may have a first end opening through the closed mouthend of the outer housing and a second opposing open end.

The method 1300 may further include dispensing an amount of aerosol precursor composition within the reservoir chamber 1304. In particular, the method may include dispensing the aerosol precursor composition into the reservoir chamber from the connecting end of the outer housing and in between the exterior surface of the outer wall of the central tube and the interior surface of the outer wall of the outer housing.

According to some aspects, the method 1300 may further include inserting a sealing member into the outer housing 1306. For example, the method may include inserting a sealing member, such as the sealing member 500 illustrated in FIGS. 7A and 7B, into the outer housing from the connecting end of the outer housing. Further, the sealing member may include a central orifice (e.g., a sealing member vapor orifice 506) configured to provide for fluid communication between any of the openings of the central tube (e.g., the opening 215 disposed at the terminal end 219 of the mouthpiece channel 216 and/or the opening 214 of the mouthpiece channel 216 disposed proximate the mouthend 202 of the reservoir housing 200), the central tube (e.g., the mouthpiece channel 216), and/or a vaporizing chamber (e.g., the vaporizing chamber 310). In particular, the method may include inserting the sealing member into the outer housing so as to engage a peripheral portion of the sealing member with the wall of the outer housing and the central orifice of the sealing member with the second open end of the central tube in a sealing arrangement. As described herein, the sealing member may include a sealing element that surrounds the circumferential periphery of the sealing member. Additionally, the central orifice of the sealing member may include an annular flange portion that provides a seat for the central tube, which the central tube may substantially abut when the central tube is in a sealing arrangement with the sealing member, as described previously herein.

The method 1300 may further include inserting a substrate member adjacent to the sealing member 1308. In particular, the substrate member may be inserted into the outer housing from the connecting end of the outer housing and may be disposed within the outer housing and substantially abut the sealing member when inserted within the outer housing. In some aspects, the method may include inserting the substrate member adjacent to the sealing member such that a substrate engaging member is inserted within a central orifice of the substrate member, as previously described herein.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
   a reservoir housing having a mouthend and a connecting end and being formed of an outer wall;
   a mouthpiece channel within the reservoir housing, the mouthpiece channel being formed of an outer wall and extending at least partially along the length of the reservoir housing from the mouthend of the reservoir housing to a terminal end, the mouthpiece channel having an opening at the mouthend of the reservoir housing and the terminal end of the mouthpiece channel;
   a sealing member in a sealing arrangement with the reservoir housing outer wall and the mouthpiece channel outer wall so as to define a reservoir chamber configured to retain an aerosol precursor composition therein, the sealing member including at least one aerosol precursor composition orifice configured for flow therethrough of the aerosol precursor composition and including a sealing member vapor orifice in communication with the opening at the terminal end of the mouthpiece channel;
   a substrate member adjacent the sealing member so as to be in fluid communication with the reservoir chamber through the sealing member, and including a substrate member vapor orifice in communication with the sealing member vapor orifice; and
   a vaporizing assembly including a liquid transport element in fluid communication with the substrate member and including a heating element in a heating arrangement with the liquid transport element.

2. The aerosol delivery device of claim 1 further comprising a connector housing configured to operably engage a power source.

3. The aerosol delivery device of claim 2, wherein the vaporizing assembly is arranged at least partially within the connector housing.

4. The aerosol delivery device of claim 2 further comprising an atomizer housing, wherein the atomizer housing comprises a vaporizing chamber in which the liquid transfer element and the heating element are disposed, the vaporizing chamber being in fluid communication with the substrate member vapor orifice, and the atomizer housing is operably engaged with the connector housing.

5. The aerosol delivery device of claim 1, wherein the sealing member vapor orifice is configured to provide for fluid communication between the mouthpiece channel and the vaporizing assembly.

6. The aerosol delivery device of claim 1, wherein the sealing member vapor orifice is configured to receive at least a portion of the mouthpiece channel therethrough.

7. The aerosol delivery device of claim 1, wherein the sealing member includes a sealing element configured to be operably engaged with the outer wall of the reservoir housing.

8. The aerosol delivery device of claim 7, wherein the sealing element includes a flange portion configured to be operably engaged with the outer wall of the mouthpiece channel.

9. The aerosol delivery device of claim 1, wherein the mouthpiece channel and the reservoir housing are substantially coaxial.

10. The aerosol delivery device of claim 1, wherein the reservoir housing further includes at least one sealing member support extending along a direction substantially parallel to a longitudinal axis of the reservoir housing and having a terminal end.

11. The aerosol delivery device of claim 10, wherein the terminal end of the mouthpiece channel extends beyond the terminal end of the sealing member support from the mouthend of the reservoir housing.

12. The aerosol delivery device of claim 10, wherein the terminal end of the sealing member support directly engages the reservoir housing.

13. The aerosol delivery device of claim 1, wherein the vaporizing assembly further includes at least one power connector operably engaging the heating element.

14. A liquid storage tank for an aerosol delivery device, the liquid storage tank comprising:
   an outer housing formed of a wall, the outer housing having a closed mouthend and an opposing end;
   a central tube interior to the outer housing and formed of a wall, the central tube having a first end opening through the closed mouthend of the outer housing and having a second, opposing open end;
   a sealing member sealingly engaging the wall of the outer housing and having a central orifice aligned with the second open end of the central tube in a sealing arrangement with the wall of the central tube; and
   a substrate member adjacent the sealing member;
   wherein the wall of the outer housing, the wall of the central tube, and the sealing member define a reservoir chamber configured for storage of an aerosol precursor composition, and the sealing member comprises at least one orifice configured for passage of the aerosol precursor composition between the reservoir chamber and the substrate member.

15. A method of manufacturing a liquid storage tank for an aerosol delivery device, the method comprising:
   providing a reservoir chamber defined, in part, by an outer housing formed of a wall and a central tube interior to the outer housing and formed of a wall, the outer housing having a closed mouthend and an opposing connecting end, the central tube having a first end opening through the closed mouthend of the outer housing and a second opposing open end;
   dispensing an aerosol precursor composition within the reservoir chamber and between the wall of the outer housing and the wall of the central tube from the connecting end of the outer housing;
   inserting a sealing member into the outer housing from the connecting end of the outer housing, the sealing member having a sealing member vapor orifice, so as to engage a peripheral portion of the sealing member with the wall of the outer housing and the sealing member vapor orifice with the second open end of the central tube in a sealing arrangement; and
   inserting a substrate member adjacent to the sealing member within the outer housing from the connecting end of the outer housing, the substrate member having a substrate member vapor orifice.

16. The method of claim 15 further comprising inserting at least a portion of a vaporizing assembly within the outer housing from the connecting end of the outer housing, the vaporizing assembly including a liquid transport element, so as to engage the liquid transport element with the substrate member disposed within the outer housing.

17. The method of claim 16, wherein the vaporizing assembly includes a heating element in a heating arrangement with the liquid transport element.

18. The method of claim 15, wherein the sealing member further includes a substrate engaging element extending from the sealing member and along a direction substantially parallel to a longitudinal axis of the outer housing, and wherein inserting the substrate member adjacent to the sealing member within the outer housing comprises inserting the substrate engaging element through at least a portion of the substrate member vapor orifice so as to provide for fluid communication between the first end opening of the central tube and the substrate member vapor orifice.

19. The method of claim 15, wherein the outer housing further includes at least one sealing member support extending along a direction substantially parallel to a longitudinal axis of the outer housing and having a terminal end, and wherein inserting the sealing member into the outer housing from the connecting end of the outer housing further includes inserting the sealing member so as to directly engage a portion of the sealing member with the terminal end of the sealing member support.

20. The method of claim 19, wherein the second opposing open end of the central tube extends beyond the terminal end of the sealing member support from the closed mouthend of the outer housing.

* * * * *